US008563754B2

(12) United States Patent
Orlow et al.

(10) Patent No.: US 8,563,754 B2
(45) Date of Patent: Oct. 22, 2013

(54) COMPOUNDS, COMPOSITIONS AND METHODS FOR PREVENTING SKIN DARKENING

(75) Inventors: Seth J. Orlow, New York, NY (US); Li Ni Komatsu, Clarksville, MD (US)

(73) Assignee: New York University, New York, NY (US)

(*) Notice: Subject to any disclaimer, the term of this patent is extended or adjusted under 35 U.S.C. 154(b) by 320 days.

(21) Appl. No.: 13/015,882

(22) Filed: Jan. 28, 2011

(65) Prior Publication Data
US 2011/0190229 A1 Aug. 4, 2011

Related U.S. Application Data

(60) Provisional application No. 61/299,335, filed on Jan. 28, 2010.

(51) Int. Cl.
*A61K 31/37* (2006.01)
*C07D 309/38* (2006.01)

(52) U.S. Cl.
CPC .................................. *A61K 31/37* (2013.01)
USPC .......................................... 549/387; 514/455

(58) Field of Classification Search
None
See application file for complete search history.

(56) References Cited

U.S. PATENT DOCUMENTS

| | | | |
|---|---|---|---|
| 3,155,591 | A | 11/1964 | Hilfer |
| 3,755,560 | A | 8/1973 | Dickert et al. |
| 3,929,678 | A | 12/1975 | Laughlin et al. |
| 3,959,461 | A | 5/1976 | Bailey et al. |
| 4,139,619 | A | 2/1979 | Chidsey, III |
| 4,387,090 | A | 6/1983 | Bolich, Jr. |
| 4,421,769 | A | 12/1983 | Dixon et al. |
| 4,684,635 | A | 8/1987 | Orentreich et al. |
| 4,822,596 | A | 4/1989 | Callingham et al. |
| 4,904,463 | A | 2/1990 | Johnson et al. |
| 5,011,681 | A | 4/1991 | Ciotti et al. |
| 5,073,371 | A | 12/1991 | Turner et al. |
| 5,073,372 | A | 12/1991 | Turner et al. |
| 5,120,532 | A | 6/1992 | Wells et al. |
| 5,132,740 | A | 7/1992 | Okamoto et al. |
| 5,151,209 | A | 9/1992 | McCall et al. |
| 5,151,210 | A | 9/1992 | Steuri et al. |
| 5,214,028 | A | 5/1993 | Tomita et al. |
| 5,389,611 | A | 2/1995 | Tomita et al. |
| 5,580,549 | A | 12/1996 | Fukuda et al. |
| 5,691,380 | A | 11/1997 | Mason et al. |
| 5,968,528 | A | 10/1999 | Deckner et al. |
| 6,123,959 | A | 9/2000 | Jones et al. |
| 6,255,324 | B1 * | 7/2001 | Heindel et al. ............ 514/314 |
| 2006/0269494 | A1 * | 11/2006 | Gupta ........................ 424/70.1 |
| 2012/0196926 | A1 * | 8/2012 | Orlow ........................ 514/452 |
| 2012/0220545 | A1 * | 8/2012 | Orlow et al. ................ 514/27 |

FOREIGN PATENT DOCUMENTS

| | | | |
|---|---|---|---|
| JP | 2004-352658 | * | 12/2004 |
| WO | 9909011 | | 2/1999 |
| WO | 9964025 | | 12/1999 |
| WO | 0062742 | | 10/2000 |
| WO | 0101131 | | 1/2001 |
| WO | 02098347 | | 12/2002 |
| WO | 2007110415 | | 10/2007 |
| WO | WO2011/068595 | * | 6/2011 |

OTHER PUBLICATIONS

Silverman et al., "The Organic Chemistry of Drug Design and Drug Action" Published 1992 by Academic Press, pp. 352-397.*
Vippagunta et al., "Crystalline Solids" Advanved Drug Delivery Reviews (2001) vol. 48 pp. 3-26.*
Jain et al., "Polymorphism in Pharmacy" Indian Drugs (1986) vol. 23 No. 6 pp. 315-329.*
Braga et al., "Making Crystals from Crystals: a green route to crystal engineering and polymorphism" Chemcomm (2005) pp. 3635-3645.*
Lieberman et al., "Pharmaceutical Dosage Forms: Tablets" published 1990 by Marcel Dekker, Inc, pp. 462-472.*
English machine translation of JP2004-352658, published Dec. 6, 2004.*
Suzuki et al., "Cancer Preventive Agents. Part 5. Anti-tumor-Promoting Effects of Coumarins and Related Compounds on Epstein-Barr Virus Activation and Two-stage Mouse Skin Carcinogenesis" Pharmaceutical Biology (2006) vol. 44 No. 3, pp. 178-182.*
Gia et al., "4'-Methyl Derivatives of 5-MOP and 5-MOA: Synthesis, Photoreactivity, and Photobiological Activity" Journal of Medicinal Chemistry (1996) vol. 39 pp. 4489-4496.*
Bundgard, H., "Design of Prodrugs", pp. 7-9, 21-24, Elsevier, Amsterdam 1985.
Niemiec et al., Pharm. Res. 12:1184-88 (1995). (Abstract).
Remington's Pharmaceutical Sciences, 17th Ed., Mack Publishing Company, Easton, PA, 1990 (supra).
Pharmaceutical Dosage Forms and Drug Delivery Systems, 6th Ed., Williams & Wilkins (1995).
McCutcheon's Detergents and Emulsifiers, North American Edition, pp. 317-324 (1986), published by Allured Publishing Corporation.
T.W. Greene and P.G.M. Wuts, "Protectingi Groups in Organic Synthesis," Second Edition, Wiley, New York, 1991.

(Continued)

*Primary Examiner* — Eric S Olson
(74) *Attorney, Agent, or Firm* — Klauber & Jackson LLC

(57) ABSTRACT

A method for preventing hyperpigmented skin, undesired pigmentation disorder of skin, or undesired darkening of skin using coumarin compounds, the use of such compounds, and compositions and formulations thereof are disclosed. In a particular embodiment, the coumarin compounds are selected from robustic acid methyl ether, scandenin, and coumophos. The compounds may be prepared as additives to pharmaceutical and cosmetic compositions, and in personal care products such as antiperspirants. In a particular embodiment extends to an antiperspirant product containing a skin darkening inhibitory amount of a compound of the invention. Also, the present skin darkening compounds may be prepared in combination with each other. The compounds, compositions and formulations of the invention may be used for the prevention of the onset or progression of conditions characterized by unwanted skin darkening, including those that may be causally related to aberrant melanogenesis activity including, by way of non-limiting example, hyperpigmentation and others.

15 Claims, 4 Drawing Sheets

(56) References Cited

OTHER PUBLICATIONS

Orlow, 1998, in The Pigmentary System: Physiology and Pathophysiology 97, Oxford University Press, New York, Nordlund et al., eds.

Fox, C.F., "Cosmetics and Toiletries," Nov. 1986, Vo. 191, pp. 101-112.

McCutcheon's, Detergents & Emulsifiers, North American Edition (1979), M.C. Publishing Co.

Fox, Charles, "An Introduction to Multiple Emulsions," Cosmetics & Toiletries, vol. 101, Nov. 1986, pp. 101-102.

* cited by examiner

Scandenin

Scandenin

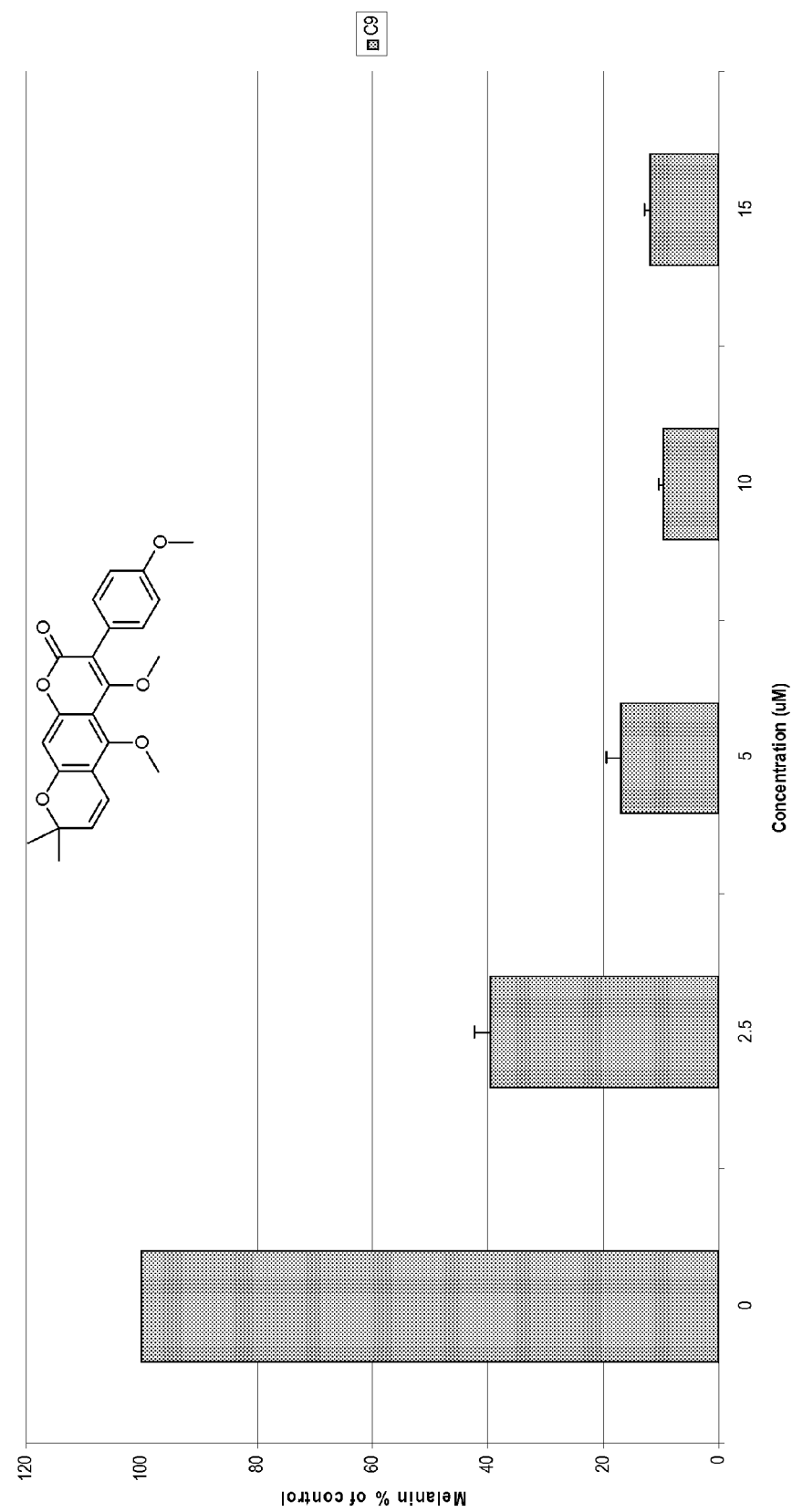

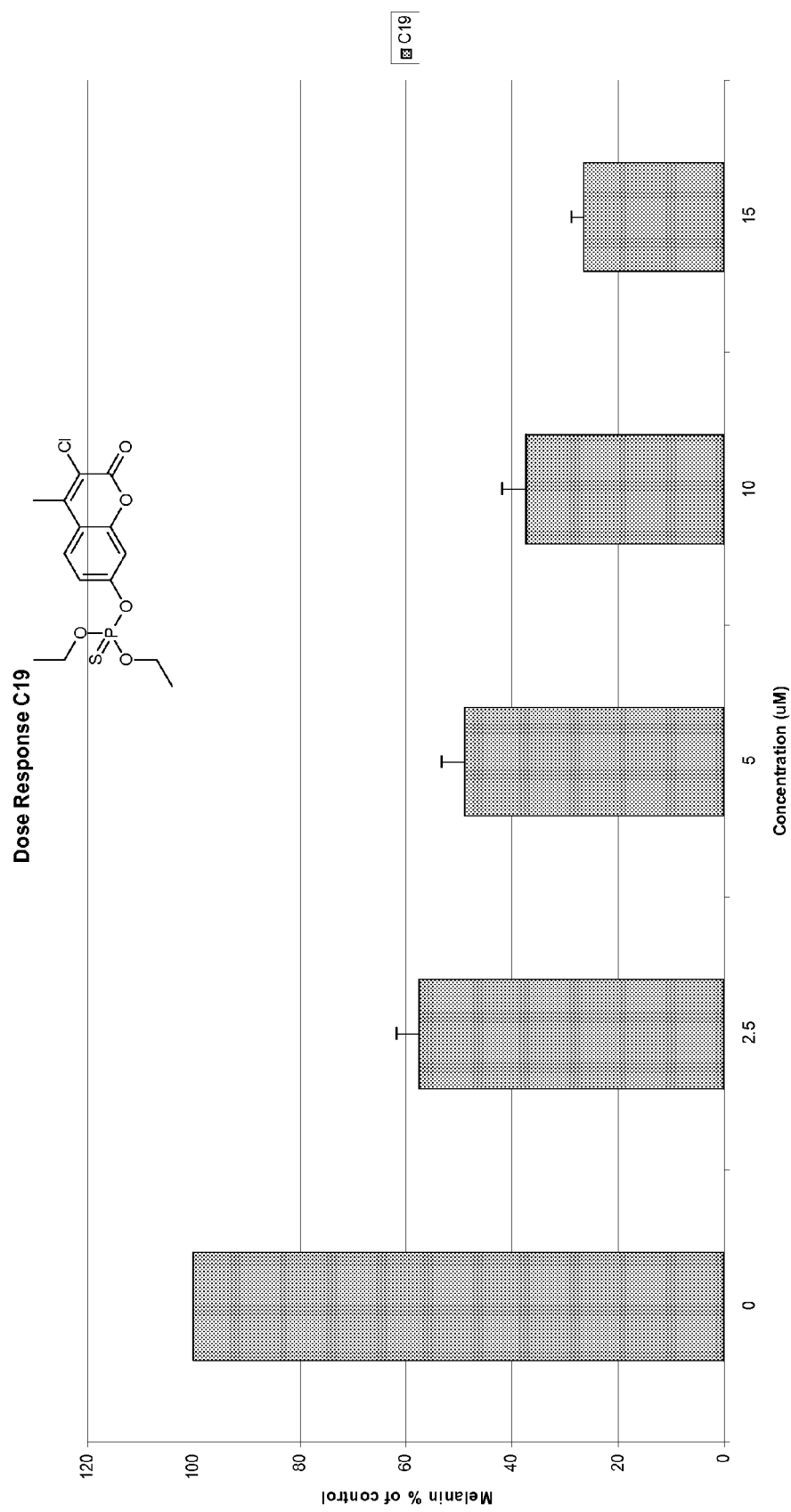

COMPOUNDS, COMPOSITIONS AND METHODS FOR PREVENTING SKIN DARKENING

RELATED APPLICATION

The present application claims the benefit under 35 U.S.C. §119 of U.S. Provisional Application Ser. No. 61/299,335 filed Jan. 28, 2010. The content of said provisional application is hereby incorporated by reference in its entirety.

GOVERNMENT RIGHTS

This invention was made in part with government support under Grant No. AR41880 awarded by the National Institute of Health. Accordingly, the United States Government has certain rights in the invention.

FIELD OF THE INVENTION

The present invention relates to the identification of particular coumarin compounds that can prevent the darkening of skin. This invention further relates to compositions and formulations containing such compounds, products containing such compounds as an additive, and to methods for preventing darkening or hyperpigmentation of skin, comprising administering an effective amount of the compounds and/or of formulations containing or comprising the compounds. As described herein, the formulations include cosmetic products and related personal care products, and would contain an effective amount of a compound of the invention therewithin. It is to be understood that such compounds may be used either alone or in combination with other compounds having the activity set forth herein.

BACKGROUND OF THE INVENTION

Several publications and patent documents are referenced in this application in order to more fully describe the state of the art to which this disclosure pertains. The disclosure of each of these publications and documents is expressly incorporated by reference herein.

One of the causes of skin darkening is the synthesis of melanin by cells known as melanocytes. Melanocytes synthesize melanin inside specialized organelles called melanosomes (reviewed in Orlow, 1998, in The Pigmentary System: Physiology and Pathophysiology 97, Oxford University Press, New York, Nordlund et al., eds). Melanosomes are formed by the fusion of two types of vesicles. Melanin is a dark biological pigment (biochrome) found in the skin, hair, feathers, scales, eyes, and some internal membranes of many animals that confers protection against ultraviolet radiation. Melanism refers to the deposition of melanin in the tissues of living animals, the chemistry of which depends on the metabolism of the amino acid tyrosine. More specifically, melanins are formed as an end product during metabolism of the amino acid tyrosine.

A particular problem that has been noted is the unwanted darkening of skin. This may result from a variety of causes, including skin conditions such as acne, and the application of certain topical compositions that cause such darkening as a side-effect. By way of example, such darkening is experienced from the application of certain deodorants or antiperspirants, or from other topical skin care products or topically administered medicaments.

While a variety of substances have been proposed for use as regulators of skin pigmentation, almost all of these substances work by either bleaching existing pigment or preventing new pigment synthesis by inhibiting the activity of tyrosinase, the principal rate limiting enzyme in the production of melanin. U.S. Pat. No. 6,123,959, for example, describes the use of aqueous compositions comprising liposomes and at least one competitive inhibitor of an enzyme involved in melanin synthesis. U.S. Pat. No. 5,132,740 describes the use of certain resorcinol derivatives as skin lightening agents. WO 99/64025 describes compositions for skin lightening which contain tyrosinase inhibiting extracts from dicotyledonous plant species indigenous to Canada. U.S. Pat. No. 5,580,549 describes an external preparation for skin lightening comprising 2-hydroxybenzoic acid derivatives and salts thereof as inhibitors of tyrosinase. WO 99/09011 describes an agent for inhibiting skin erythema and/or skin pigmentation, containing at least one carbostyril derivative and salts thereof. U.S. Pat. Nos. 5,214,028 and 5,389,611, describe lactoferrin hydrolyzates for use as tyrosinase inhibitory agents.

In WO 02 98347, Manga describes methods for identifying compounds that alter melanogenesis in melanogenic cells, more particularly, compounds that inhibit or enhance P protein function. This method is based, in part, on the observation that P protein function is required for proper cellular localization of tyrosinase and other melanosomal proteins, and is required for both full tyrosinase activity and melanogenesis in melanogenic cell types.

Orlow et al. describe screens for identifying compounds that inhibit or increase melanogenesis in melanogenic cells. See WO 01 1131. These studies were based upon the discovery that some compounds that inhibit melanogenesis do so by causing a mislocalization of tyrosinase, the key enzyme in melanin synthesis. Also, WO 2007/110415 is directed to the preparation of particular diacetyl trimers, and their use in compositions for cosmetic or therapeutic use, for decreasing melanin synthesis and concentration, for the lightening of skin.

The above disclosures are predicated on a method of action that proposes to modulate cellular activity, and that by doing so, would function to modify melanin content and thereby, the color or hue of the skin. The present invention focuses instead on the darkening that results from a variety of seemingly disparate origins, and seeks only to prevent such darkening, and not to modulate melanogenesis.

As described herein, the present invention addresses the need for novel agents that are capable of preventing the darkening phenomenon. Accordingly, the present invention provides compounds for use in skin care and personal care formulations, and corresponding methods for preventing hyperpigmented skin, undesired pigmentation disorder of skin, or undesired darkening of skin comprising administering such compounds, or formulations or compositions containing an effective amount of the inventive compounds.

SUMMARY OF THE INVENTION

In a first aspect, the present invention is directed to compounds that are capable of inhibiting or preventing unwanted skin darkening. Such compounds may be incorporated into topical products for personal care, such as anti-perspirants, deodorants, perfumes, lotions, and the like, as well as corresponding formulations for pharmaceutical use.

In a further aspect of the invention, a method for preventing the hyperpigmentation or undesired darkening of skin comprises administering an effective amount of a compound of formula I

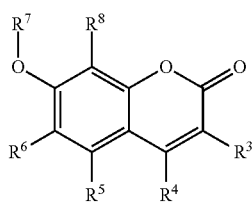

or a pharmaceutically acceptable salt, solvate or prodrug thereof, and stereoisomers, tautomers and isotopic variants thereof; and wherein $R^3$ is selected from H, halo, substituted or unsubstituted alkyl, substituted or unsubstituted alkenyl, or substituted or unsubstituted aryl; and substituted or unsubstituted heteroaryl;

$R^4$ is selected from H, halo, hydroxy, alkoxy, alkenyloxy, substituted or unsubstituted alkyl, substituted or unsubstituted alkenyl, and substituted or unsubstituted phenyl;

each $R^5$, $R^{6'}$ and $R^8$ is independently selected from H, halo, hydroxy, alkoxy, alkenyloxy, substituted or unsubstituted alkyl, substituted or unsubstituted alkenyl, and substituted or unsubstituted phenyl;

$R^7$ is selected from H, halo, hydroxy, alkoxy, alkenyloxy, substituted or unsubstituted alkyl, substituted or unsubstituted alkenyl, or heterocycloalkyl; or $R^7$ is —P(=O)(alkoxy)$_2$, or —P(=S)(alkoxy)$_2$; or $R^6$ and $R^7$ or $R^7$ and $R^8$ are joined to form a 5- or 6-membered heterocycloalkyl or heterocycloalkenyl; and the heterocycloalkyl or heterocycloalkenyl is unsubstituted or substituted with one more groups selected from alkyl, alkenyl, hydroxyalkyl, acyloxyalkyl, hydroxy, and alkoxy; and provided that i) when $R^3$ is H; then $R^8$ is substituted or unsubstituted alkenyl;

ii) the compound is other than robustic acid; and iii) when each of $R^3$, $R^4$, $R^5$, and $R^6$ is H; and $R^8$ is 3-methylbut-2-enyl; then $R^7$ is other than Me.

In one particular embodiment, with respect to formula I, the compound is formula VIIa (robustic acid methyl ether):

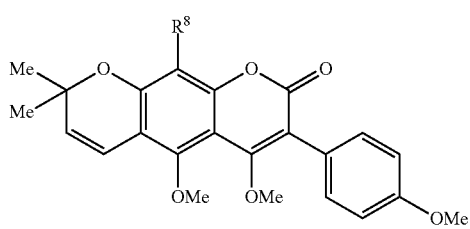

or a pharmaceutically acceptable salts, solvates, isomers, tautomers, metabolites, analogs, isotopic variants or prodrugs thereof.

In another particular embodiment, with respect to formula I, the compound is formula VIIb (scandenin):

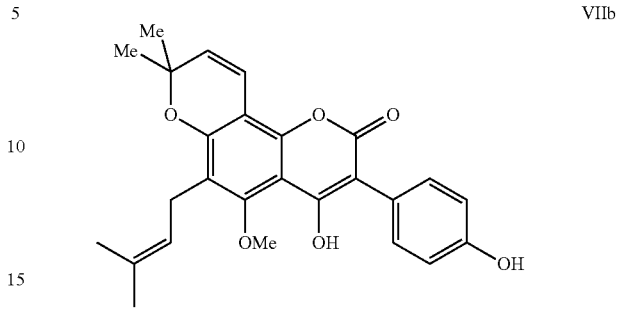

or a pharmaceutically acceptable salts, solvates, isomers, tautomers, metabolites, analogs, isotopic variants or prodrugs thereof.

Another aspect of this invention relates to the use of a compound of the invention in a therapeutic method, a pharmaceutical composition, and the manufacture of such composition, useful for the prevention of either the onset or the progression of conditions involving aberrant or unwanted increases in pigmentation or darkening of skin as may be attributable to e.g. hyperpigmentation, acne, melasma and chloasma. This invention also relates to processes for the preparation of the compounds of the invention.

In a further aspect, the present invention provides compositions, including cosmetic formulations, comprising a compound or compounds of the invention, and a suitable biocompatible or bioinert carrier, excipient or diluent. In this aspect of the invention, the cosmetic or pharmaceutical composition can comprise one or more of the compounds described herein. Moreover, the compounds of the present invention useful in the cosmetic and pharmaceutical compositions and treatment methods disclosed herein, are all pharmaceutically acceptable as prepared and used.

In a further aspect, the present invention provides personal care products, such as deodorant and/or anti-perspirant compositions, that include or contain an effective amount of a compound of the invention, to prevent the skin darkening that is a side-effect of the use of such products. Such a product can comprise an antiperspirant and/or a deodorant active, in liquid, solid (particulate) or aerosol form, together with a carrier providing either a solid or a liquid form to the product, and conventional additives, such as gellants, oils, and the like.

In a further aspect, the present invention provides compositions comprising a combination of a compound of the invention with various compounds or agents that may have a like effect. In this aspect of the invention, the compositions can comprise one or more of the compounds described herein, individually or in combination with each other.

Other objects and advantages will become apparent to those skilled in the art from a consideration of the ensuing detailed description, which proceeds with reference to the following illustrative drawings.

BRIEF DESCRIPTION OF THE DRAWINGS

FIG. 3 is a graph of the individual dose response testing of Robustic acid methyl ether, a particular compound of the invention.

FIG. 4 is a graph of the individual dose response testing of Coumophos, a particular compound of the invention.

DETAILED DESCRIPTION OF THE INVENTION

Definitions

Figure 1:
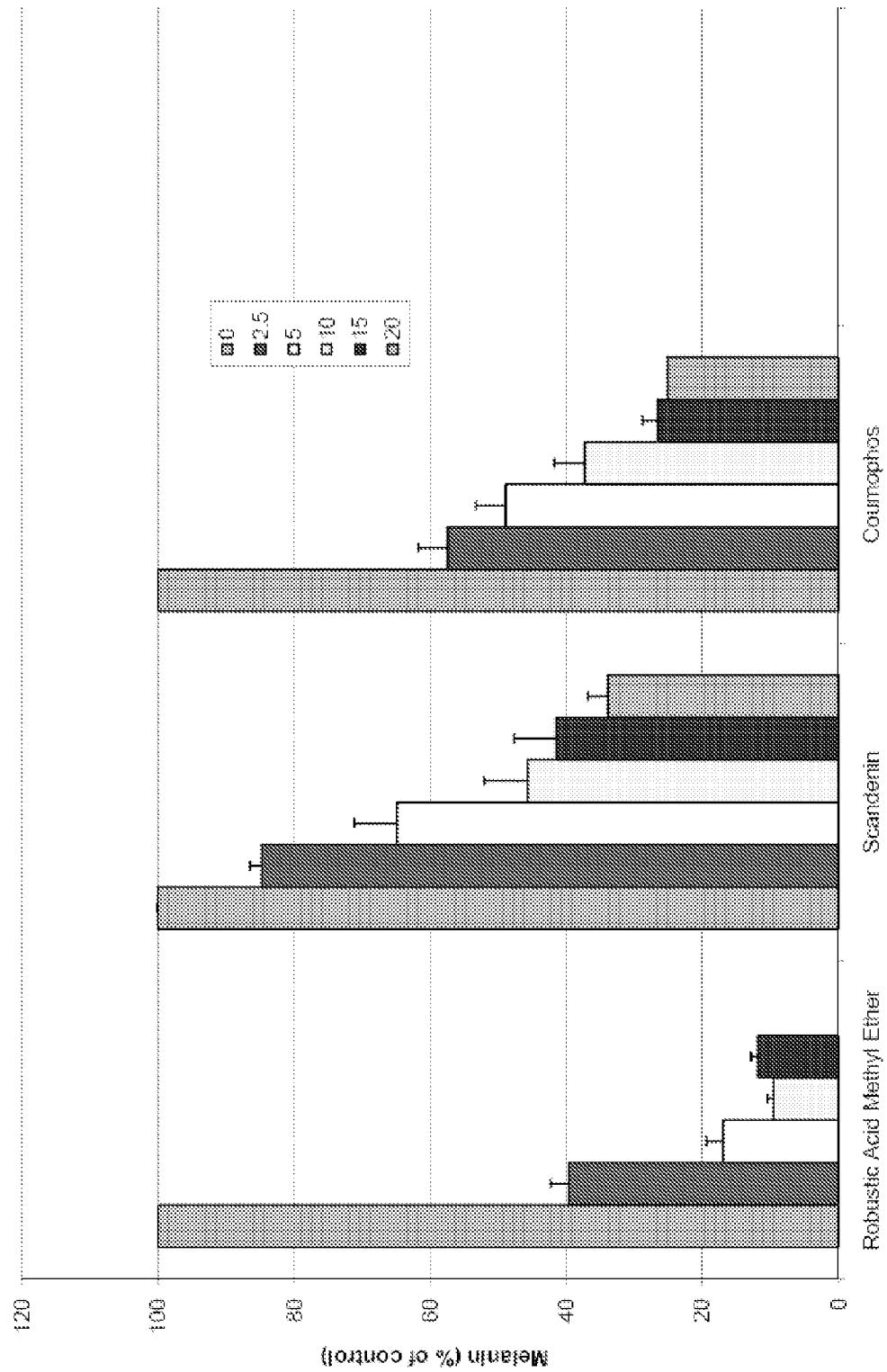
FIG. 1 is a graph of the results of comparative dose-response testing of compounds of the invention as inhibitors of skin darkening.

When describing the compounds, pharmaceutical and/or cosmetic compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

"Acyl" refers to a group or radical —C(O)$R^{20}$, where $R^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a group or radical —N$R^{21}$C(O)$R^{22}$, where $R^{21}$ is hydrogen, alkyl, cycloalkyl, cycloheteroalkyl, aryl, arylalkyl, heteroalkyl, heteroaryl, heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group or radical —OC(O)$R^{23}$ where $R^{23}$ is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —O$R^{24}$ where $R^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —N$R^{25}$C(O)$R^{26}$ where $R^{25}$ is hydrogen, alkyl, aryl or cycloalkyl, and $R^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, iso-propyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically or alkynically unsaturated hydrocarbyl groups particularly having 2 to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group $R^{27}$—C(O)—, where $R^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR$^{28}$R$^{29}$, wherein each of R$^{28}$ and R$^{29}$ are independently selected from hydrogen and alkyl.

"Arylamino" refers to the group aryl-NR$^{30}$R$^{31}$, wherein each of R$^{30}$ and R$^{31}$ are independently selected from hydrogen, aryl and heteroaryl.

"Alkoxyamino" refers to a radical —N(H)OR$^{32}$ where R$^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —NR$^{33}$R$^{34}$ where R$^{33}$ represents an alkyl or cycloalkyl group and R$^{34}$ is an aryl as defined herein.

"Alkylsulfonyl" refers to a radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R$^{35}$ where R$^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR$^{35}$ where R$^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R$^{36}$)$_2$ where each R$^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R$^{36}$)$_2$ is an amino group.

"Aminocarbonyl" refers to the group —C(O)NR$^{37}$R$^{37}$ where each R$^{37}$ is independently hydrogen, alkyl, aryl and cycloalkyl, or where the R$^{37}$ groups are joined to form an alkylene group.

"Aminocarbonylamino" refers to the group —NR$^{38}$C(O)NR$^{38}$R$^{38}$ where each R$^{38}$ is independently hydrogen, alkyl, aryl or cycloalkyl, or where two R groups are joined to form an alkylene group.

"Aminocarbonyloxy" refers to the group —OC(O)NR$^{39}$R$^{39}$ where each R$^{39}$ is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —NHR$^{40}$ where R$^{40}$ represents an aryl group as defined herein.

"Aryloxycarbonyl" refers to a radical —C(O)—O-aryl where aryl is as defined herein.

"Arylsulfonyl" refers to a radical —S(O)$_2$R$^{41}$ where R$^{41}$ is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N($R^{42}$)$_2$ where each $R^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_{27}$—.

"Cycloalkoxy" refers to the group —O$R^{43}$ where $R^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —N$R^{44}R^{45}$ where $R^{44}$ and $R^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to —X, —$R^{46}$, —O$^-$, =O, —O$R^{46}$, —S$R^{46}$, S$^-$, =S=N$R^{46}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2R^{46}$, —OS(O$_2$)O$^-$, —OS(O)$_2R^{46}$, —P(O)(O$^-$)$_2$, —P(O)(O$R^{46}$)(O$^-$), —OP(O)(O$R^{46}$)(O$R^{47}$), —C(O)$R^{46}$, —C(S)$R^{46}$, —C(O)O$R^{46}$, —C(O)N$R^{46}R^{47}$, —C(O)O$^-$, —C(S)O$R^{46}$, —N$R^{48}$C(O)N$R^{46}R^{47}$, —N$R^{48}$C(S)N$R^{46}R^{47}$, —N$R^{49}$C(N$R^{48}$)N$R^{46}R^{47}$ and —C(N$R^{48}$)N$R^{46}R^{47}$, where each X is independently a halogen; each $R^{46}$, $R^{47}$, $R^{48}$ and $R^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —N$R^{50}R^{51}$, —C(O)$R^{50}$ or —S(O)$_2R^{50}$ or optionally $R^{50}$ and $R^{51}$ together with the atom to which they are both attached form a cycloheteroalkyl or substituted cycloheteroalkyl ring; and $R^{50}$ and $R^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

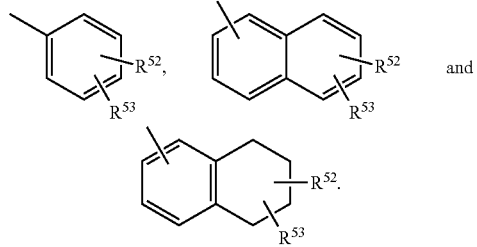

In these formulae one of $R^{52}$ and $R^{53}$ may be hydrogen and at least one of $R^{52}$ and $R^{53}$ is each independently selected from alkyl, alkenyl, alkynyl, cycloheteroalkyl, alkanoyl, alkoxy, aryloxy, heteroaryloxy, alkylamino, arylamino, heteroarylamino, N$R^{54}$CO$R^{55}$, N$R^{54}$SO$R^{55}$, N$R^{54}$SO$_2R^{57}$, COOalkyl, COOaryl, CONR$^{54}R^{55}$, CONR$^{54}$O$R^{55}$, N$R^{54}R^{55}$, SO$_2$N$R^{54}R^{55}$, S-alkyl, S-alkyl, SOalkyl, SO$_2$alkyl, Saryl, SOaryl, SO$_2$aryl; or $R^{52}$ and $R^{53}$ may be joined to form a cyclic ring (saturated or unsaturated) from 5 to 8 atoms, optionally containing one or more heteroatoms selected from the group N, O or S. $R^{54}$, $R^{55}$, and $R^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

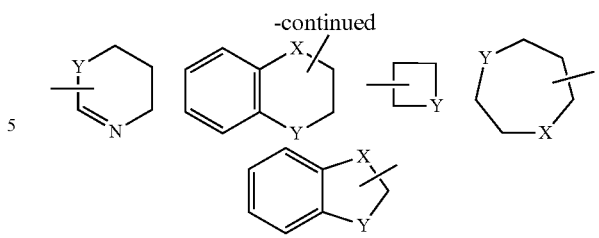

wherein each Y is selected from carbonyl, N, $NR^{58}$, O, and S; and $R^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

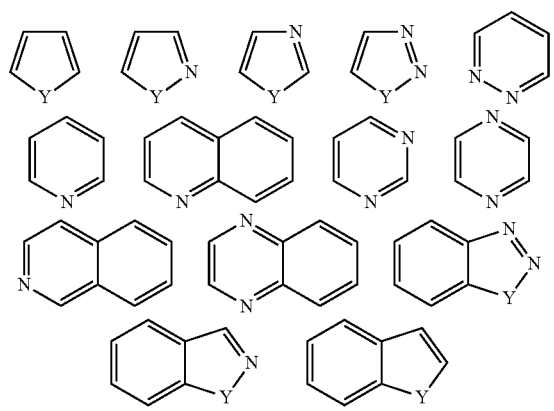

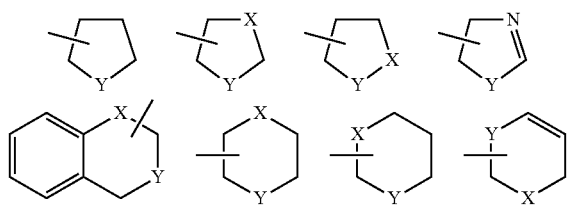

-continued wherein each X is selected from $CR^{58}$, $CR^{58}{}_2$, $NR^{58}$, O and S; and each Y is selected from $NR^{58}$, O and S; and $R^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

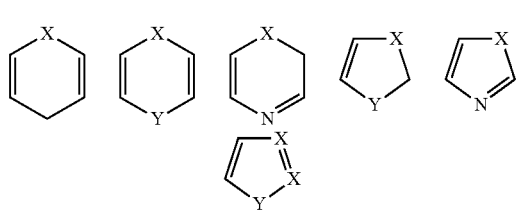

wherein each X is selected from $CR^{58}$, $CR^{58}{}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

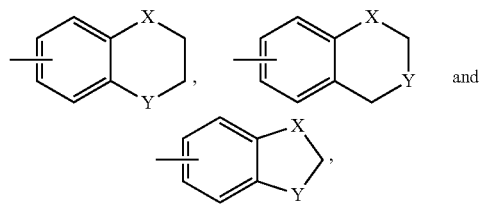

wherein each X is selected from $CR^{58}{}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an $R^4$ in a $R^{4c}$ group present as substituents directly on the ring or rings of the compounds of this invention, or that may be present as a substituent in any "substituted" aryl and aliphatic groups present in the compounds.

Examples of hetero substituents include:
-halo,
—$NO_2$, —$NH_2$, —$NHR^{59}$, —$N(R^{59})_2$,
—NRCOR, —$NR^{59}SOR^{59}$, —$NR^{59}SO_2R^{59}$, OH, CN,
—$CO_2H$,
—$R^{59}$—OH, —O—$R^{59}$, —$COOR^{59}$,
—$CON(R^{59})_2$, —$CONROR^{59}$,
—$SO_3H$, —$R^{59}$—S, —$SO_2N(R^{59})_2$,
—$S(O)R^{59}$, —$S(O)_2R^{59}$
wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

"Dihydroxyphosphoryl" refers to the radical —$PO(OH)_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)$NH_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —$SR^{60}$ where $R^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —$S(O_2)$—. "Substituted sulfonyl" refers to a radical such as $R^{61}$—$(O_2)S$— wherein $R^{61}$ is any substituent described herein. "Aminosulfonyl" or "Sulfonamide" refers to the radical $H_2N(O_2)S$—, and "substituted aminosulfonyl" "substituted sulfonamide" refers to a radical such as $R^{62}_2N(O_2)S$— wherein each $R^{62}$ is independently any substituent described herein.

"Sulfone" refers to the group —$SO_2R^{63}$. In particular embodiments, $R^{63}$ is selected from H, lower alkyl, alkyl, aryl and heteroaryl.

"Thioaryloxy" refers to the group —$SR^{64}$ where $R^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

As used herein, "mammal" refers to any member of the higher vertebrate animals comprising the class Mammalia, which includes, but is not limited to, humans.

As used herein, the term "melanogenesis inhibitor" is used to describe a compound or an agent, extract of a natural material, or the like, that is known or is identified herein as possessing the ability to inhibit melanogenesis in a melanocyte.

As used herein, an "amount effective" shall mean an amount sufficient to cover the region of skin, hair, fur, or wool surface where a change in pigmentation is desired.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like.

The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject not yet exposed to or predisposed to the disease, and not yet experiencing or displaying symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease or a condition, is sufficient to effect such treatment for the disease or condition. The "therapeutically effective amount" can vary depending on the compound, the disease or condition and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same. In a still further embodiment, "treating" or "treatment" refers to administration of the compound or composition of the invention for cosmetic purposes.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H/D$, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

As described herein, the present invention relates to the identification of compounds that prevent or inhibit skin darkening. This invention also relates to methods for preventing and/or treating conditions that may include or involve skin darkening, such as aberrant pigmentation, including hyperpigmentation of all etiologies, uneven pigmentation, and the like, using the compounds and compositions of the invention. This invention further relates to methods for preventing hyperpigmented skin, undesired pigmentation disorder of skin, or undesired darkening of skin comprising administering an effective amount of a coumarin compound as defined herein.

In accordance with the present invention, a plurality of compounds has been identified that are capable of inhibiting skin darkening. These compounds, which were not previously identified as possessing such a capability, are listed herein. Accordingly, the present invention is directed to their use in inhibiting or preventing darkening in in vitro and in vivo applications. With respect to in vitro applications, test-tube based and additional cell-based assays may be used to test the ability of modified versions and/or derivatives of compounds listed herein to prevent darkening. In vivo applications are directed to the administration of at least one of the novel inhibitor compounds listed herein to a subject in need thereof to prevent increases in pigmentation levels for prophylactic, therapeutic and/or cosmetic purposes.

One aspect of the invention provides a method for preventing hyperpigmented skin, undesired pigmentation disorder of skin, or undesired darkening of skin comprising administering an effective amount of a compound of formula I

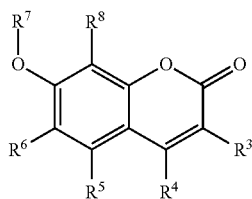

I or a pharmaceutically acceptable salt, solvate or prodrug thereof, and stereoisomers, tautomers and isotopic variants thereof; and wherein $R^3$ is selected from H, halo, substituted or unsubstituted alkyl, substituted or unsubstituted alkenyl, or substituted or unsubstituted aryl; and substituted or unsubstituted heteroaryl;

$R^4$ is selected from H, halo, hydroxy, alkoxy, alkenyloxy, substituted or unsubstituted alkyl, substituted or unsubstituted alkenyl, and substituted or unsubstituted phenyl;

each $R^5$, $R^{6'}$ and $R^8$ is independently selected from H, halo, hydroxy, alkoxy, alkenyloxy, substituted or unsubstituted alkyl, substituted or unsubstituted alkenyl, and substituted or unsubstituted phenyl;

$R^7$ is selected from H, halo, hydroxy, alkoxy, alkenyloxy, substituted or unsubstituted alkyl, substituted or unsubstituted alkenyl, or heterocycloalkyl; or $R^7$ is —P(=O)(alkoxy)$_2$, or —P(=S)(alkoxy)$_2$; or $R^6$ and $R^7$ or $R^7$ and $R^8$ are joined to form a 5- or 6-membered heterocycloalkyl or heterocycloalkenyl; and the heterocycloalkyl or heterocycloalkenyl is unsubstituted or substituted with one more groups selected from alkyl, alkenyl, hydroxyalkyl, acyloxyalkyl, hydroxy, and alkoxy; and provided that iv) when $R^3$ is H; then $R^8$ is substituted or unsubstituted alkenyl;

v) the compound is other than robustic acid; and vi) when each of $R^3$, $R^4$, $R^5$, and $R^6$ is H; and $R^8$ is 3-methylbut-2-enyl; then $R^7$ is other than Me.

In one embodiment of the invention, the invention provides a method for preventing hyperpigmented skin comprising administering an effective amount of a compound of formula I.

In another embodiment of the invention, the invention provides a method for preventing undesired pigmentation disorder of skin comprising administering an effective amount of a compound of formula I.

In another embodiment of the invention, the invention provides a method for preventing undesired darkening of skin comprising administering an effective amount of a compound of formula I.

In one embodiment of the invention, with respect to formula I, $R^7$ is selected from H, substituted or unsubstituted alkyl, and substituted or unsubstituted alkenyl.

In one embodiment of the invention, with respect to formula I, $R^3$ is H, Cl, alkyl, or substituted or unsubstituted phenyl.

In another embodiment of the invention, with respect to formula I, $R^3$ is H, Cl, Me, phenyl, 4-hydroxyphenyl, or 4-methoxyphenyl.

In one embodiment of the invention, with respect to formula I, $R^4$ is H, Cl, alkyl, or substituted or unsubstituted phenyl.

In another embodiment of the invention, with respect to formula I, $R^4$ is H, Cl, Me, phenyl, or 4-methoxyphenyl.

In one embodiment of the invention, with respect to formula I, $R^5$ is H, Cl, alkyl, hydroxy, or alkoxy.

In another embodiment of the invention, with respect to formula I, $R^5$ is H, Cl, Me, OH, or OMe.

In one embodiment of the invention, with respect to formula I, $R^6$ is H, Cl, alkyl, alkenyl, hydroxy, alkoxy, or alkenyloxy.

In another embodiment of the invention, with respect to formula I, $R^6$ is H, Cl, OH, OMe, 3-methylbut-2-enyl, or 3-methylbut-2-enyloxy.

In one particular embodiment of the invention, with respect to formula I, $R^6$ is H, H, or OMe.

In one embodiment of the invention, with respect to formula I, $R^8$ is H, Cl, alkyl, alkenyl, hydroxy, alkoxy, or alkenyloxy.

In another embodiment of the invention, with respect to formula I, $R^8$ is H, Cl, OH, OMe, 3-methylbut-2-enyl, or 3-methylbut-2-enyloxy.

In one particular embodiment of the invention, with respect to formula I, $R^8$ is H, OH, OMe, or 3-methylbut-2-enyl.

In one particular embodiment of the invention, with respect to formula I, $R^7$ is H, Me, 3-methylbut-2-enyl, P(=O)(OEt)$_2$, P(=S)(OEt)$_2$, or 6-hydroxymethyl-3,4,5-trihydroxypyran-2-yl.

In one particular embodiment of the invention, with respect to formula I, each $R^3$, $R^4$, $R^5$, $R^6$ is H; $R^7$ is as described for formula I; and $R^8$ is substituted or unsubstituted alkenyl. In another embodiment, $R^8$ is 3-methylbut-2-enyl; and $R^7$ is other than Me.

In one particular embodiment of the invention, with respect to formula I, each $R^3$, $R^4$, $R^5$, $R^6$ is H; $R^8$ is substituted or unsubstituted alkenyl; and $R^7$ is H, Me, 3-methylbut-2-enyl, P(=O)(OEt)$_2$, P(=S)(OEt)$_2$, or 6-hydroxymethyl-3,4,5-trihydroxypyran-2-yl. In another embodiment, $R^8$ is substituted or unsubstituted alkenyl; and $R^7$ is Me. In yet another particular embodiment, $R^8$ is 3-methylbut-2-enyl and $R^7$ is Me.

In one particular embodiment of the invention, with respect to formula I, $R^4$, $R^5$, $R^6$, $R^7$ and $R^8$ are as described for formula I; and $R^3$ is Cl.

In one particular embodiment of the invention, with respect to formula I, $R^4$, $R^5$, $R^6$, and $R^8$ are as described for formula I; and $R^3$ is Cl; and $R^7$ is H, Me, 3-methylbut-2-enyl, P(=O)(OEt)$_2$, P(=S)(OEt)$_2$, or 6-hydroxymethyl-3,4,5-trihydroxypyran-2-yl. In another embodiment, $R^7$ is Me, or $P(=S)(OEt)_2$. In yet another embodiment, $R^7$ is Me, or $P(=S)(OEt)_2$.

In one particular embodiment of the invention, with respect to formula I, the compound is coumophos.

In one embodiment of the invention, with respect to formula I, $R^6$ and $R^7$ are joined to form a 5- or 6-membered heterocycloalkyl or heterocycloalkenyl; and the heterocycloalkyl or heterocycloalkenyl is unsubstituted or substituted with one more groups selected from alkyl, alkenyl, hydroxyalkyl, acyloxyalkyl, hydroxy, and alkoxy.

In one embodiment of the invention, with respect to formula I, $R^7$ and $R^8$ are joined to form a 5- or 6-membered heterocycloalkyl or heterocycloalkenyl; and the heterocycloalkyl or heterocycloalkenyl is unsubstituted or substituted with one more groups selected from alkyl, alkenyl, hydroxyalkyl, acyloxyalkyl, hydroxy, and alkoxy.

In one embodiment of the invention, with respect to formula I, the compound is according to formulae IIa, IIb, IIc, or IId:

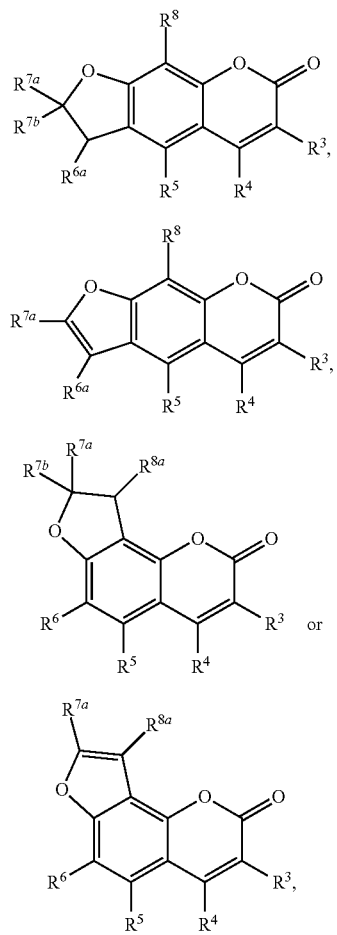

or a pharmaceutically acceptable salt, solvate or prodrug thereof, and stereoisomers, tautomers and isotopic variants thereof; and wherein $R^4$, $R^5$, and $R^6$ are as described for formula I;

$R^3$ is selected from halo, substituted or unsubstituted alkyl, substituted or unsubstituted alkenyl, or substituted or unsubstituted phenyl;

$R^8$ is selected from H, halo, hydroxy, alkoxy, alkenyloxy, substituted or unsubstituted alkyl, substituted or unsubstituted alkenyl, or substituted or unsubstituted phenyl; and each $R^{6a}$, $R^{7a}$, $R^{7b}$, and $R^{8a}$ is independently selected from H, alkyl, hydroxyalkyl, or alkenyl.

In one embodiment of the invention, with respect to formula I, the compound is according to formulae IIIa, IIIb, IIIc or IIId:

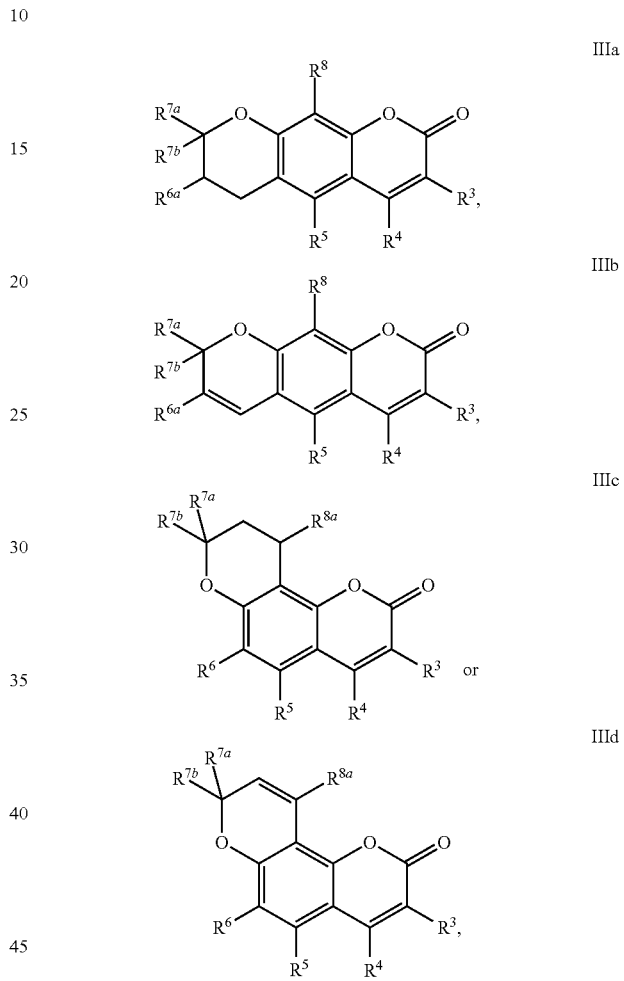

or a pharmaceutically acceptable salt, solvate or prodrug thereof, and stereoisomers, tautomers and isotopic variants thereof; and wherein $R^4$, $R^5$, and $R^6$ are as described for formula I;

$R^3$ is selected from halo, substituted or unsubstituted alkyl, substituted or unsubstituted alkenyl, or substituted or unsubstituted phenyl;

$R^8$ is selected from H, halo, hydroxy, alkoxy, alkenyloxy, substituted or unsubstituted alkyl, substituted or unsubstituted alkenyl, or substituted or unsubstituted phenyl; and each $R^{6a}$, $R^{7a}$ and $R^{7b}$ is independently selected from H, alkyl, hydroxyalkyl, or alkenyl.

In one embodiment of the invention, with respect to formulae IIa, IIc and IIIa-IIId, $R^{7a}$ is H or Me.

In one embodiment of the invention, with respect to formulae IIa, IIc and IIIa-IIId, $R^{7b}$ is H or Me.

In one particular embodiment, each of $R^{7a}$ and $R^{7b}$ is Me.

In one embodiment of the invention, with respect to formulae IIc, IId, IIIc, or IIId, $R^{8a}$ is H or Me.

In one embodiment of the invention, with respect to formulae IIc, IId, IIIc, or IIId, $R^6$ is H, Me, OH, OMe, 3-methylbuten-2-yl; or 3-methylbuten-2-yloxy.

In one embodiment of the invention, with respect to formula I, the compound is according to formula IV:

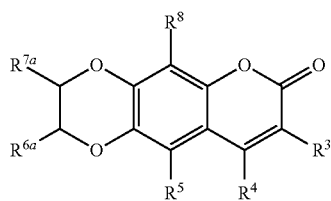

IV or a pharmaceutically acceptable salt, solvate or prodrug thereof, and stereoisomers, tautomers and isotopic variants thereof; and wherein $R^4$, and $R^5$ are as described for formula I;

$R^3$ is selected from halo, substituted or unsubstituted alkyl, substituted or unsubstituted alkenyl, or substituted or unsubstituted phenyl;

$R^8$ is selected from H, halo, hydroxy, alkoxy, alkenyloxy, substituted or unsubstituted alkyl, substituted or unsubstituted alkenyl, or substituted or unsubstituted phenyl; and each $R^{6a}$ and $R^{7a}$ is independently selected from H, alkyl, or alkenyl.

In one embodiment of the invention, with respect to formulae I-IV, $R^4$ is H, Cl, alkyl, hydroxy, alkoxy, or substituted or unsubstituted phenyl.

In one embodiment of the invention, with respect to formulae I-IV, $R^4$ is H, Me, OH, OMe, or 4-methoxyphenyl.

In one embodiment of the invention, with respect to formulae I-IV, $R^4$ is OH or OMe.

In one embodiment of the invention, with respect to formulae I-IV, $R^{6a}$ is H or Me.

In one embodiment of the invention, with respect to formulae I-IV, $R^{6a}$ is H.

In one embodiment of the invention, with respect to formulae I-IV, $R^{7a}$ is H or Me.

In one embodiment of the invention, with respect to formulae I-IV, $R^{7b}$ is H or Me.

In one embodiment of the invention, with respect to formulae I-IV, each $R^{7a}$ and $R^{7b}$ is H or Me.

In one embodiment of the invention, with respect to formulae I-IV, each $R^{7a}$ and $R^{7b}$ is Me.

In one embodiment of the invention, with respect to formulae I-IV, $R^{8a}$ is H or Me.

In one embodiment of the invention, with respect to formula I, the compound is of formulae Va, Vb, Vc, or Vd:

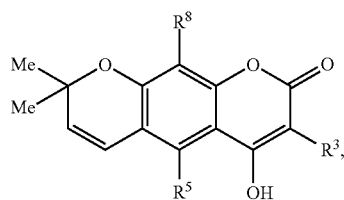

Va

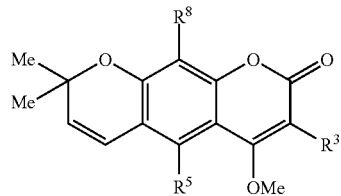

Vb

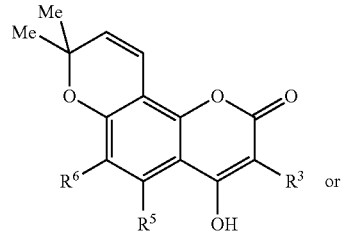

Vc

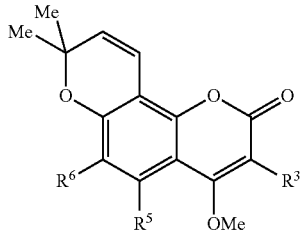

Vd or a pharmaceutically acceptable salt, solvate or prodrug thereof, and stereoisomers, tautomers and isotopic variants thereof; and wherein $R^4$, $R^5$, and $R^6$ are as described for formula I;

$R^3$ is selected from halo, substituted or unsubstituted alkyl, substituted or unsubstituted alkenyl, or substituted or unsubstituted phenyl;

$R^8$ is selected from H, halo, hydroxy, alkoxy, alkenyloxy, substituted or unsubstituted alkyl, substituted or unsubstituted alkenyl, or substituted or unsubstituted phenyl.

In one embodiment of the invention, with respect to formulae I-Vd, $R^5$ is H, Cl, alkyl, hydroxy, or alkoxy.

In one embodiment of the invention, with respect to formulae I-Vd, $R^5$ is H, Cl, Me, OH, or OMe.

In one embodiment of the invention, with respect to formulae I-Vd, $R^5$ is OH or OMe.

In one embodiment of the invention, with respect to formulae I-Vd, $R^8$ is H, Cl, alkyl, alkenyl, hydroxy, alkoxy, or alkenyloxy.

In one embodiment of the invention, with respect to formulae I-Vd, $R^8$ is H, Cl, OH, OMe, 3-methylbut-2-enyl, or 3-methylbut-2-enyloxy.

In one embodiment of the invention, with respect to formulae I-Vd, $R^8$ is H or 3-methylbut-2-enyl.

In one embodiment of the invention, with respect to formulae I-Vd, $R^6$ is H, Cl, alkyl, alkenyl, hydroxy, alkoxy, or alkenyloxy.

In one embodiment of the invention, with respect to formulae I-Vd, $R^6$ is H, Cl, OH, OMe, 3-methylbut-2-enyl, or 3-methylbut-2-enyloxy.

In one embodiment of the invention, with respect to formulae I-Vd, $R^6$ is 3-methylbut-2-enyl.

In one embodiment of the invention, with respect to formula I, the compound is of formulae VIa, VIb, VIc, or VId:

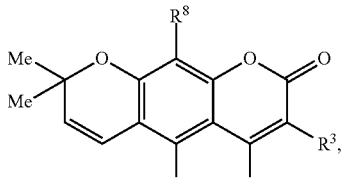
VIa

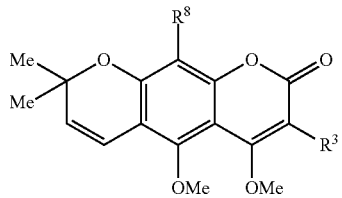
VIb

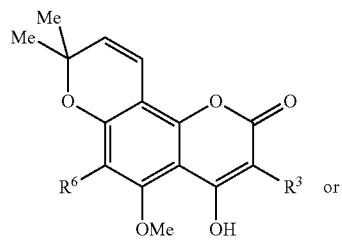
VIc

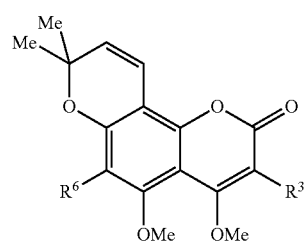
VId or a pharmaceutically acceptable salt, solvate or prodrug thereof, and stereoisomers, tautomers and isotopic variants thereof; and wherein $R^3$ is selected from halo, substituted or unsubstituted alkyl, substituted or unsubstituted alkenyl, or substituted or unsubstituted phenyl.

In one embodiment of the invention, with respect to formulae I-VId, $R^3$ is Cl, alkyl, or substituted or unsubstituted phenyl.

In one embodiment of the invention, with respect to formulae I-VId, $R^3$ is Me, phenyl, 4-hydroxyphenyl, 3,4-dihydroxyphenyl, 4-methoxyphenyl, or 3,4-dimethoxyphenyl.

In one embodiment of the invention, with respect to formula I, the compound is of formulae VIIa, or VIIb:

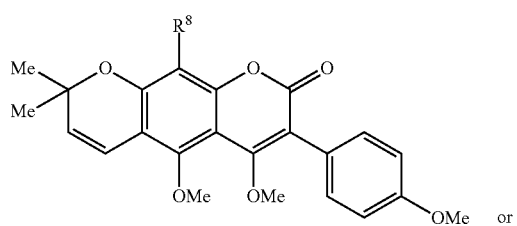
VIIa

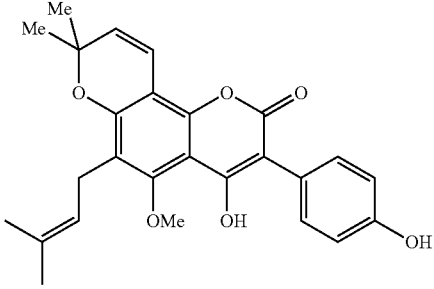
VIIb or a pharmaceutically acceptable salt, solvate or prodrug thereof, and stereoisomers, tautomers and isotopic variants thereof.

In one particular embodiment, with respect to formula I, the compound is formula VIIa (robustic acid methyl ether):

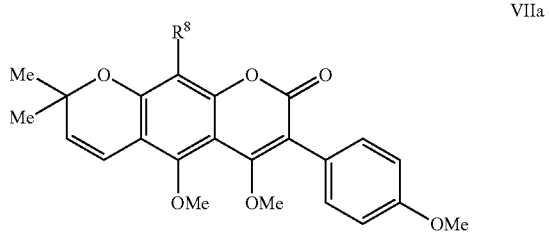
VIIa or a pharmaceutically acceptable salts, solvates, isomers, tautomers, metabolites, analogs, isotopic variants or prodrugs thereof.

In another particular embodiment, with respect to formula I, the compound is formula VIIb (scandenin):

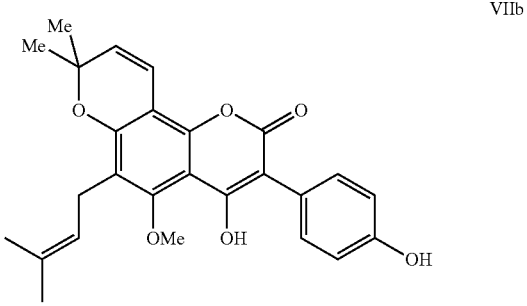 [SMILES: COc1c(CC=C(C)C)c2c(c3oc(=O)c(-c4ccc(O)cc4)c(O)c13)C=CC(C)(C)O2]
VIIb or a pharmaceutically acceptable salt, solvate, isomer, tautomer, metabolite, analog, isotopic variant or prodrug thereof.

In one particular embodiment, with respect to formula I, the compound is selected from the compounds listed in Table 1.

In another particular embodiment of the invention, with respect to formula I, the compound is pachyrrhizin, robustic acid methyl ether, or scandenin In one embodiment of the invention, with respect to formula I, the compound is robustic acid methyl ether.

In one embodiment of the invention, with respect to formula I, the compound is scandenin.

In one embodiment of the invention, with respect to formula I, the compound is pachyrrhizin.

In one embodiment, with respect to the method of the invention, the method comprises a step of contacting skin with a) a composition comprising a compound as set forth in any of formulae I-VIIb in a sufficient amount to prevent hyperpigmented skin, undesired pigmentation disorder of skin, or undesired darkening of skin, and b) an acceptable carrier.

In other aspect the invention, the invention provides a composition for preventing hyperpigmented skin, undesired pigmentation disorder of skin, or undesired darkening of skin comprising an amount of a compound according to formulae I-VIIb effective to inhibit such conditions. The compositions may be for cosmetic or dermatological use, and may be selected from lotions, crèmes, gels, sprays, and may include emollients, perfumes, and the like.

In one embodiment of the invention, with respect to the composition, the composition is selected from skin lotion, skin softener, skin toner, astringent, lotion, milk lotion, moisture lotion, nutrient lotion, massage cream, nutrient cream, moisture cream, hand cream, foundation, essence, nutrient essence, pack, cleansing foam, cleansing lotion, cleansing cream, body lotion, body cleanser, treatment or beauty solution.

In yet another aspect the invention, the invention provides a combination to prevent hyperpigmented skin, undesired pigmentation disorder of skin, or undesired darkening of skin consisting of a compound according to formulae I-VIIb and a like-acting agent.

In one embodiment of the invention, with respect to the combination, the like acting agent is selected from a cosmetic ingredient and a pharmacologically active agent.

In one embodiment of the invention, with respect to the combination, the said pharmacologically active agent is selected from another melanogenesis inhibitor.

In one embodiment of the invention, with respect to the method, composition or combination as described above, the hyperpigmented skin, undesired pigmentation disorder of skin, or undesired darkening of skin is caused by environmental or physiological conditions.

In one embodiment of the invention, with respect to the method, composition or combination as described above, the hyperpigmented skin, undesired pigmentation disorder of skin, or undesired darkening of skin is due to the use of personal care products.

In one embodiment of the invention, with respect to the method, composition or combination as described above, the hyperpigmented skin, undesired pigmentation disorder of skin, or undesired darkening of skin is age spots, freckles, drug-induced hyperpigmentation, post-inflammatory hyperpigmentation as seen in acne, melasma or chloasma.

In one embodiment of the invention, with respect to the method, composition or combination as described above, the skin is mammalian skin.

In one embodiment of the invention, with respect to the method, composition or combination as described above, the skin is human skin.

A further aspect of the invention extends to a formulation that comprises a combination of a compound with respect to formulae I-VIIb, and a like-acting agent. In a particular embodiment, the like acting agent is selected from a cosmetic ingredient and a pharmacologically active agent.

In a particular embodiment of the combination just described, a pharmaceutical composition is prepared that is useful to treat a disease for which a melanogenesis inhibitor is indicated, which comprises a therapeutically effective amount of the combination, wherein the like acting agent is a pharmacologically active agent.

In a further embodiment of the combination described above, a topical formulation is prepared that comprises a composition for cosmetic or dermatological use, which composition comprises a cosmetically and/or dermatologically effective amount of the combination stated above, wherein the like acting agent is a cosmetically active agent.

The methods and compositions of the present invention contemplate the use of one or more of the compounds listed herein as an active ingredient(s) for various uses. In a particular embodiment, the active ingredient(s) is combined with an acceptable carrier to form a topical formulation for application to the skin, for example, for cosmetic and/or therapeutic dermatological uses. Topical formulations may include ointments, lotions, pastes, creams, gels, drops, suppositories, sprays, liquids, shampoos, powders and transdermal patches. Thickeners, diluents, emulsifiers, dispersing aids or binders may be used as needed. Preferably, one function of the carrier is to enhance skin penetration of the active ingredient(s), and should be capable of delivering the active ingredient(s) to melanocytes under in vivo conditions. Suitable carriers are well known to skilled practitioners, and include liposomes, ethanol, dimethylsulfoxide (DMSO), petroleum jelly (petrolatum), mineral oil (liquid petrolatum), water, dimethylformamide, dekaoxyethylene-oleylether, oleic acid, 2-pyrrolidone and Azone® brand penetration enhancer (Upjohn). A particular composition may be formulated to include an active ingredient(s) as described in Table I, with one of 2-pyrrolidone, oleic acid and/or Azone® added to enhance penetration, solubilized in a base of water, ethanol, propanol and/or propylene glycol.

As indicated above, vehicles comprising liposomes may be used for topical delivery of some of the compositions of the invention. Depending on the composition, and at the discretion of a skilled practitioner, such liposomes may be non-ionic and contain a) glycerol dilaurate (preferably in an amount of between about 5% and about 70% by weight); b) compounds having the steroid backbone found in cholesterol (preferably in an amount of between about 5% and about 45% by weight); and c) one or more fatty acid ethers having from about 12 to about 18 carbon atoms preferably in an amount of between about 5% and about 70% by weight collectively), wherein the constituent compounds of the liposomes are preferably in a ratio of about 37.5:12.5:33.3:16.7. For some compositions, liposomes comprised of glycerol dilaurate/cholesterol/polyoxyethylene-10-stearyl ether/polyoxyethylene-9-lauryl ether (GDL liposomes) are preferred. Liposomes may be present in an amount, based upon the total volume of the composition, of from about 10 mg/mL to about 100 mg/mL, and more preferably from about 20 mg/mL to about 50 mg/mL. A ratio of about 37.5:12.5:33.3:16.7 may be used to particular advantage. Suitable liposomes may be prepared in accordance with standard methods commonly used in the art.

The above described composition may be prepared by combining the desired components in a suitable container and mixing them under ambient conditions in any conventional high shear mixing means well known in the art for non-ionic liposome preparations, such as those disclosed in Niemiec et al. (Pharm. Res. 12:1184-88 (1995)), which is incorporated by reference herein in its entirety. The presence of such liposomes enhances the depigmenting capabilities of some compositions.

Other formulations may contain, for example, soybean milk or other liquid formulations derived directly from legumes or other suitable plant. Such a formulation may, for example, contain a large proportion of soybean milk, an emulsifier that maintains the physical stability of the soybean milk, and, optionally a chelating agent, preservatives, emollients, humectants and/or thickeners or gelling agents.

Oil-in-water emulsions, water-in-oil emulsions, solvent-based formulations and aqueous gels known to those of skill in the art may also be utilized as vehicles for the delivery of the compositions of this invention.

Depending on the specific application, the compositions of the present invention may also include other active ingredients, as well as inert or inactive ingredients. In such alternative embodiments, the topically active pharmaceutical or cosmetic composition may be optionally combined with other ingredients such as moisturizers, cosmetic adjuvants, surfactants, foaming agents, conditioners, humectants, fragrances, viscosifiers, buffering agents, preservatives, sunscreens and the like.

The amount of the aforementioned examples of additional active ingredients for skin treatment (one or more compounds) in the formulations according to the invention may vary in accordance with the end use of the product and in accordance with accepted norms for such formulations. Exemplary ranges may be from about 0.01 to about 30 wt. %, particularly from about 0.01 to about 20 wt. %, and more particularly from about 0.01 to about 5 wt. %, based on the total weight of the preparation. The foregoing ranges are presented by way of illustration and not limitation.

In certain aspects, the present invention provides prodrugs and derivatives of the compounds of the invention. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

The present invention also relates to the cosmetologically and pharmaceutically acceptable acid addition and base salts of any of the aforementioned compounds of formulae I-VIIb. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1-methylene-bis-(2-hydroxy-3-naphthoate)) salts.

The compounds useful according to the invention that are basic in nature are capable of forming a wide variety of different salts with various inorganic and organic acids. Although such salts must be pharmaceutically acceptable for administration to animals, it is often desirable in practice to initially isolate a compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds useful according to the invention that are acidic in nature are capable of forming base salts with various pharmaceutically acceptable cations. Examples of such salts include the alkali metal and alkaline earth metal salts and, particularly, the sodium and potassium salts. These salts can be prepared by conventional techniques. The chemical bases that are used as reagents to prepare the pharmaceutically acceptable base salts of this invention are those that form non-toxic base salts with the acidic compounds of formula I. Such non-toxic base salts include those derived from such pharmaceutically acceptable cations as sodium, potassium, calcium and magnesium, etc. These salts can easily be prepared by treating the corresponding acidic compounds with an aqueous solution containing the desired pharmaceutically acceptable cations, and then evaporating the resulting solution to dryness, preferably under reduced pressure. Alternatively, they can also be prepared by mixing lower alkanolic solutions of the acidic compounds and the desired alkali metal alkoxide together, and then evaporating the resulting solution to dryness, as described above. In either case, stoichiometric quantities of reagents are preferably employed in order to ensure completeness of reaction and maximum yields of the desired final products.

The compounds useful according to the invention, and their pharmaceutically acceptable salts, are useful for the prevention of disorders of human pigmentation, including solar and simple lentigines (including age/liver spots), melasma/chloasma and postinflammatory hyper-pigmentation.

The appropriate dose regimen, the amount of each dose administered, and specific intervals between doses of the active compound will depend upon the particular active compound employed, the condition of the patient being treated, and the nature and severity of the disorder or condition being treated. Preferably, the active compound is administered in an amount and at an interval that results in the desired treatment of or improvement in the disorder or condition being treated.

Although methods and materials similar or equivalent to those described herein can be used in the practice or testing of the invention, preferred methods and materials are described below. The materials, methods, and examples are illustrative only and not intended to be limiting. Other features and advantages of the invention will be apparent from the detailed description, examples, and the claims.

Rational Drug Design

Compounds identified by the methods of the invention or compounds disclosed herein may serve as the basis for molecular modeling techniques for the design of chemical analogs that are more effective. For example, chemical analogs of any of the compounds listed herein can be created using these or other modeling techniques. Examples of molecular modeling systems are the CHARM (Polygen Corporation, Waltham, Mass.) and QUANTA (Molecular Simulations Inc., San Diego, Calif.) programs. CHARM performs the energy minimization and molecular dynamics functions. QUANTA performs the construction, graphic modeling and analysis of molecular structure, and allows interactive construction, modification, visualization, and analysis of the behavior of molecules with each other.

For example, compounds of the present invention can further be used to design more effective analogs using modeling packages such as Ludi, Insight II, $C^2$-Minimizer and Affinity (Molecular Simulations Inc., San Diego, Calif.). A particularly preferred modeling package is MacroModel (Columbia University, New York, N.Y.).

The compounds of the present invention can further be used as the basis for developing a rational combinatorial library. Such a library can also be screened to identify more effective compounds. While the nature of the combinatorial library is dependent on various factors such as the particular compound chosen from the preferred compounds of the present invention to form the basis of the library, as well as the desire to synthesize the library using a resin, it will be recognized that the compounds of the present invention provide requisite data suitable for combinatorial design programs such as $C^2$-QSAR (Molecular Simulations Inc., San Diego, Calif.).

Methods of Inhibiting Skin Darkening

As stated above, the compounds of the invention can be used to treat animals or, preferably, humans that have diseases, conditions, or disorders that may be caused at least in part, by the production or overproduction of melanin. Such diseases, conditions, or disorders include those that can be characterized by discolorations of the skin or hair such as, for example, hyperpigmentation caused by inflammation or from diseases such as melasma, or brown spots such as "cafe au lait" macules.

For the purposes of this application, the terms "treatment", "therapeutic use", and "medicinal use" shall refer to any and all uses of the compositions of the invention which remedy a disease state or one or more symptoms, or otherwise prevent, hinder, or retard, the progression of disease or one or more other undesirable symptoms in any way whatsoever.

The invention further provides methods and pharmaceutical compositions for inhibiting skin darkening comprising the use of the present compounds either alone or in combination with other, like-acting agents.

Personal Care Products and Applications

In addition to pharmaceutical uses, and in a particular embodiment of the invention, the compounds, compositions and methods are intended for use in personal care topical products that can include the skin darkening inhibitor compounds. Such products include antiperspirant and deodorant compositions, the preparation and composition of which are illustrated in U.S. Pat. No. 7,504,091, the disclosure of which is incorporated herein by reference in its entirety. Thus for example, a representative antiperspirant includes the active ingredient, a carrier that may be solid or liquid, and that is generally water-immiscible, and other additives such as gellants, perfumes, colorants and the like.

In a particular aspect, the present invention comprises the incorporation of the present skin darkening inhibitor compounds into personal care products such as deodorants, and the preparation of such products with the skin darkening inhibitor compounds included therein. Generally, personal care products such as antiperspirant and deodorant compositions have as their function and objective, to reduce the flow of sweat and to mask, absorb, improve and/or reduce the unpleasant odor resulting from the decomposition of human sweat by bacteria. Specific compositions prepared for use as antiperspirants and/or deodorants will include an active ingredient that is often known as an "antiperspirant aluminum salt." As used herein, the term "antiperspirant aluminum salt" means any salt or any aluminum complex that has the effect of reducing or limiting the flow of sweat. Numerous aluminum salts are known in the art, and the following discussion offers a non-limiting review.

Aluminum salts that may be used include aluminum halohydrates; aluminum zirconium halohydrates; and complexes of zirconium hydroxychloride and aluminum hydroxychloride with an amino acid, such as those commonly known as "ZAG complexes," for example, as described in U.S. Pat. No. 3,792,068, the disclosure of which is incorporated herein by reference in its entirety.

Specific aluminum salts include aluminum chlorohydrate in activated or unactivated form, aluminum chlorohydrex, aluminum chlorohydrex polyethylene glycol complex, aluminum chlorohydrex propylene glycol complex, aluminum dichlorohydrate, aluminum dichlorohydrex polyethylene glycol complex, aluminum dichlorohydrex propylene glycol complex, aluminum sesquichlorohydrate, aluminum sesquichlorohydrex polyethylene glycol complex, aluminum sesquichlorohydrex propylene glycol complex, and aluminum sulfate buffered with sodium aluminum lactate. Also included are aluminum zirconium double salts such as aluminum zirconium octachlorohydrate, aluminum zirconium pentachlorohydrate, aluminum zirconium tetrachlorohydrate, and aluminum zirconium trichlorohydrate.

Complexes of zirconium hydroxychloride and of aluminum hydroxychloride with an amino acid are generally known as ZAG when the amino acid is glycine. ZAG complexes include aluminum zirconium octachlorohydrex glycine, aluminum zirconium pentachlorohydrex glycine, aluminum zirconium tetrachlorohydrex glycine, and aluminum zirconium trichlorohydrex glycine complexes. For example, aluminum chlorohydrate in activated or unactivated form may be used.

The antiperspirant aluminum salts may be present in the compositions of the invention in an amount ranging from about 0.5% to 25% by weight relative to the total weight of the composition. Zinc gluconate may be present in the compositions in an amount ranging from about 0.1% to 10% by weight, such as from 0.1% to 7% by weight, relative to the total weight of the composition.

In order to provide a composition effective for antiperspirant purposes, it is preferred that the aluminum salt is present in the composition of the invention in amounts corresponding to a total aluminum content of up to 3 gram atoms of Al per kilogram of composition, in particular from 1.0 to 2.0 gram atoms Al per kg composition.

The carrier or carriers in which the antiperspirant aluminum salt is dissolved and/or dispersed may be any of the carriers traditionally used for incorporation into antiperspirant compositions. Thus, the carrier may be a liquid, a gel, a semisolid or a powder. Liquid carriers may be alcohols, glycols, fats, fatty acid esters, fatty acids, paraffins, liquid polymers (such as silicone oil), for example ethyl alcohol, isopropyl myristate, glycerine, propylene glycol, etc. as well as mixtures thereof. A gel carrier may be an alcohol or another of the above mentioned liquid carriers such as ethyl alcohol containing a cellulose derivative such as hydroxypropyl cellulose. A semisolid carrier may be a polyglycol, a paraffin (for example vaseline), fats, or any of the above mentioned liquids containing a polymer such as liquid paraffin containing dissolved polyethylene (marketed under the trade name Plastibase). A solid carrier may be talc, starch, kaolin etc.

Deodorant compositions may be prepared in a variety of forms depending upon the particular end use or application, such as for use as cosmetic product. The deodorant compositions may thus be prepared as lotions, creams or fluid gels distributed as an aerosol spray, in a pump-dispenser bottle, as a roll-on, in the form of thick creams distributed in tubes or a grille, in the form of wands (sticks). The compositions thus prepared may include ingredients generally used in products of this type, that are well known to those of skill in the art, such ingredients however, chosen on the basis that they do not interfere with the aluminum salt and the zinc gluconate described above.

The deodorant compositions provided herein may optionally comprise at least one aqueous phase. They may be formulated as aqueous lotions, water-in-oil emulsions, oil-in-water emulsions, or as multiple emulsions such as oil-in-water-in-oil and water-in-oil-in-water triple emulsions. Such emulsions are known and described, for example, by C. F. Fox in "Cosmetics and Toiletries," November 1986, Vol. 101, pages 101-112.

The aqueous phase of these compositions generally comprises water and generally at least one water-soluble or water-miscible solvent. Water-soluble and water-miscible solvents include short-chain monoalcohols, such as $C_1$-$C_4$ monoalcohols, for example ethanol and isopropanol; as well as diols and polyols, for example, ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, and sorbitol. For example, propylene glycol and glycerol may be used.

The antiperspirant compositions may optionally be anhydrous. As used herein, the term "anhydrous" refers to a composition with a free or added water content of less than 3% by weight, for example with an added water content of less than 1% by weight, relative to the total weight of the composition.

The compositions may optionally comprise at least one water-immiscible organic liquid phase. This phase generally comprises at least one hydrophobic compound that renders the phase water-immiscible. The water-immiscible organic liquid phase is liquid (in the absence of a structuring agent) at room temperature (25° C.) The water-immiscible organic liquid phase generally comprises an oil or mixture of oils and comprises at least 80% of compounds with a vapor pressure not exceeding 4 kPa (30 mmHg) at 25° C.

The water-immiscible organic liquid phase may optionally comprise at least one volatile or non-volatile, silicone-based or hydrocarbon-based emollient oil. Suitable emollient oils include those described in U.S. Pat. Nos. 4,822,596 and 4,904,463, the entire disclosures of which are incorporated herein by reference.

As is known in the art, volatile silicones are compounds that are volatile at room temperature. Volatile silicones include cyclic and linear volatile dimethylsiloxane silicones with chains comprising from 3 to 9 silicone-based residues. Cyclomethicones D4, D5, and D6 may be used.

Correspondingly, non-volatile silicones are compounds with a low vapor pressure at room temperature. Non-volatile silicones include polyalkylsiloxanes, such as polyalkylsiloxanes, for example linear polydimethylsiloxanes and dimethicones, sold by Dow Corning under the name "Dow Corning 245 Fluid;" polyalkylarylsiloxanes, such as polymethylphenylsiloxanes sold by Dow Corning under the name "Dow Corning 556 Fluid;" and polyether and siloxane copolymer, for example, dimethicone copolyols.

Non-volatile emollient oils that may be used in the compositions include hydrocarbon-based derivatives; mineral oils; fatty alcohols; esters of $C_3$-$C_{18}$ alcohols with $C_3$-$C_{18}$ acids; esters of benzoic acid with $C_{12}$-$C_{18}$ alcohols and mixtures thereof; $C_2$-$C_6$ polyols, for example, glycerol, propylene glycol, and sorbitol; and polyalkylene glycol polymers. The emollient oils may be present in the composition in an amount ranging from 1% to 50% by weight, for example, from 5% to 40% by weight, relative to the total weight of the composition.

The deodorant compositions may further comprise at least one additional deodorant active agent, for example, bacteriostatic agents and bactericidal agents such as 2,4,4'-trichloro-2'-hydroxydiphenyl ether (Triclosan), 2,4-dichloro-2'-hydroxydiphenyl ether, 3',4',5'-trichlorosalicylanilide, 1-(3',4'-dichlorophenyl)-3-(4'-chlorophenyl)urea (Triclocarban), and 3,7,11-trimethyldodeca-2,5,10-trienol (Farnesol); quaternary ammonium salts, for example, cetyltrimethylammonium salts and cetylpyridinium salts; chlorhexidine and salts thereof; diglyceryl monocaprate, diglyceryl monolaurate, and glyceryl monolaurate; and polyhexamethylene biguanide salts.

At least one suspension agent may be used to improve the homogeneity of the compositions. Suspension agents include hydrophobic-modified montmorillonite clays, for example, hydrophobic-modified bentonites and hectorites. Examples include stearalkonium bentonite (CTFA name, product of reaction of bentonite and the quaternary ammonium stearalkonium chloride), such as the commercial product sold under the name Tixogel MP 250 by Sud Chemie Rheologicals, United Catalysts Inc.; and the product disteardimonium hectorite (CTFA name, product of reaction of hectorite and of distearyldimonium chloride) sold under the name Bentone 38 or Bentone Gel by Elementis Specialities. The suspension agents may be present in an amount ranging from 0.1% to 5% by weight, for example from 0.2% to 2% by weight, relative to the total weight of the composition.

The compositions may optionally further comprise at least one filler, such as an organic powder. Fillers that may be used in the compositions include organic powders. As used herein, the term "organic powder" means any solid that is insoluble in the medium at room temperature (25° C.).

Organic powders that may be used in the compositions include polyamide particles such as those sold under the name Orgasol by Atochem; polyethylene powders; microspheres based on acrylic copolymers, such as those made of ethylene glycol dimethacrylate/lauryl methacrylate copolymer, sold by Dow Corning under the name Polytrap; polymethyl methacrylate microspheres, sold under the name Microsphere M-100 by Matsumoto and under the name Covabead LH85 by Wackherr; ethylene-acrylate copolymer powders, for example, those sold under the name Flobeads by Sumitomo Seika Chemicals; expanded powders such as hollow microspheres and microspheres formed from a terpolymer of vinylidene chloride, of acrylonitrile and of methacrylate and sold under the name Expancel by Kemanord Plast under the references 551 DE 12 (particle size of about 12 µm and density of 40 kg/m³), 551 DE 20 (particle size of about 30 µm and a density of 65 kg/m³) and 551 DE 50 (particle size of about 40 µm), and the microspheres sold under the name Micropearl F 80 ED by Matsumoto; powders of natural organic materials such as starch powders, for example, of corn starch, wheat starch, and rice starch, which may or may not be crosslinked, such as the starch powder crosslinked with octenylsuccinate anhydride, sold under the name Dry-Flo by National Starch; silicone resin microbeads such as those sold under the name Tospearl by Toshiba Silicone, for example, Tospearl 240; amino acid powders such as the lauroyllysine powder sold under the name Amihope LL-11 by Ajinomoto; particles of wax microdispersion, which have mean sizes of less than 1 µm, for example, ranging from 0.02 µm to 1 µm, and which comprise a wax or a mixture of waxes, such as the products sold under the name Aquacer by Byk Cera and Aquacer 520 (mixture of synthetic and natural waxes), Aquacer 514 and 513 (polyethylene wax), Aquacer 511 (polymer wax), the products sold under the name Jonwax 120 by Johnson Polymer (mixture of polyethylene wax and paraffin wax), and under the name Ceraflour 961 by Byk Cera (micronized modified polyethylene wax); and mixtures thereof.

The compositions may also include adjuvants useful for personal care and cosmetic applications, that are chosen from waxes, softeners, antioxidants, opacifiers, stabilizers, moisturizers, vitamins, fragrances, bactericides, preserving agents, polymers, fragrances, thickeners, propellants, and any other ingredient usually used in formulations of this type.

As stated above, when the compositions are to be prepared in solid form, a variety of known ingredients are included. For example, such ingredients include Waxes include animal, fossil, plant, mineral, and synthetic waxes, for example, beeswaxes, carnauba wax, candelilla wax, sugar cane wax, Japan wax, ozokerites, montan wax, microcrystalline waxes, paraffins, silicone waxes, and resins.

The thickeners, which may be nonionic, include modified and unmodified guar gums and celluloses, such as hydroxypropyl guar gum and cetylhydroxyethylcellulose, silicas, for example, Bentone Gel MIO sold by NL Industries, and Veegum Ultra sold by Polyplastic.

The compositions may optionally further comprise at least one other agent for structuring or gelling the water-immiscible organic liquid phase of the composition, such as linear solid fatty alcohols and/or waxes; fatty acids and salts thereof, for example, stearic acid, sodium stearate, and 12-hydroxystearic acid; dibenzylidene alditols (DBS); lanosterol; N-acylamino acid derivatives; di- and tricarboxylic acid derivatives, for example, alkyl-N,N'-dialkylsuccin-amides, e.g., dodecyl-N,N'-dibutylsuccinamide; elastomeric polyorganosiloxanes such as those described in PCT Patent Application No. WO 97/44010, the disclosure of which is incorporated herein in its entirety.

The compositions according may also be pressurized and may be packaged in an aerosol device. Suitable and exemplary aerosol devices may comprise: (a) a container comprising a composition as defined above, (b) at least one propellant, and (c) a means for distributing the composition.

The propellants generally used in products of this type, which are well known to those skilled in the art, include, for example, dimethyl ether (DME) and volatile hydrocarbons such as n-butane, propane, and isobutane, and mixtures thereof, optionally with at least one chlorohydrocarbon and/or fluorohydrocarbon. Examples include the compounds sold by Dupont de Nemours under the names Freon® and Dymel®), for example, monofluorotrichloromethane, difluorodichloromethane, tetrafluorodichloroethane and 1,1-difluoroethane sold under the trade name Dymel 152 A by Dupont. Carbon dioxide, nitrous oxide, nitrogen, and compressed air may also be used as propellants.

The composition comprising the deodorant active agents and the propellants may be in the same compartment or in different compartments in the aerosol container. The concentration of propellant generally ranges from 5% to 95% by pressurized weight, for example from 50% to 85% by weight, relative to the total weight of the pressurized composition.

The distribution means, which forms a part of the aerosol device, generally comprises a distribution valve controlled by a distribution head comprising a nozzle via which the aerosol composition is vaporized. The container comprising the pressurized composition may be opaque or transparent. It may be made of glass, of polymeric material or of metal, optionally coated with a coat of protective varnish.

Cosmetic Applications

The personal care application of the present invention extends to the use of the compounds, compositions and methods of the current invention for cosmetic purposes. Cosmetic applications for methods of the present invention include the topical application of compositions containing one or more compounds to prevent the alteration by darkening, of the visual appearance of skin or hair. Occurrences in the skin or hair of noticeable but undesired pigmentation such as, from melanin overproduction, can be prevented using the methods of the present invention. Suitable formulations for these purposes can be prepared by those skilled in the art, and such details of preparation are considered within the scope of the present invention.

Methods of Administration

The compounds of the invention can be administered topically, e.g., as patches, ointments, creams, gels, lotions, solutions, foams, masks or transdermal administration.

If in vivo use is contemplated, the composition is preferably of high purity and substantially free of potentially harmful contaminants, e.g., at least National Food (NF) grade, generally at least analytical grade, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

Useful pharmaceutical dosage forms for administration of the present compounds are described below.

The pharmaceutical compositions can be applied directly to the skin. Alternatively, they can be delivered by various transdermal drug delivery systems, such as transdermal patches as known in the art. For example, for topical administration, the active ingredient can be formulated in a solution, gel, lotion, ointment, cream, suspension, foam, mask, paste, liniment, powder, tincture, aerosol, patch, or the like in a pharmaceutically or cosmetically acceptable form by methods well known in the art. The composition can be any of a variety of forms common in the pharmaceutical or cosmetic arts for topical application to animals or humans, including solutions, lotions, sprays, creams, ointments, salves, gels, etc., as described below. Preferred agents are those that are viscous enough to remain on the treated area, those that do not readily evaporate, and/or those that are easily removed by rinsing with water, optionally with the aid of soaps, cleansers and/or shampoos. Actual methods for preparing topical formulations are known or apparent to those skilled in the art, and are described in detail in *Remington's Pharmaceutical Sciences*, 1990 (supra); and *Pharmaceutical Dosage Forms and Drug Delivery Systems*, 6th ed., Williams & Wilkins (1995).

In order to enhance the percutaneous absorption of the active ingredients, one or more of a number of agents can be added in the topical formulations including, but not limited to, dimethylsulfoxide, dimethylacetamide, dimethylformamide, surfactants, azone, alcohol, acetone, propylene glycol and polyethylene glycol. In addition, physical methods can also be used to enhance transdermal penetration such as, e.g., by iontophoresis or sonophoresis. Alternatively, or in addition, liposomes may be employed.

A topically applied composition of the invention contains a pharmaceutically effective amount of at least one of the compounds of the invention as described herein, and those ingredients as are necessary for use as a carrier, such as an emulsion, a cream, an ointment, an ophthalmic ointment, an aqueous solution, a lotion or an aerosol. Non-limiting examples of such carriers are described in more detail below and may be found in International Patent Publication WO 00/62742, published Oct. 26, 2000, U.S. Pat. No. 5,691,380 to Mason et al., issued on Nov. 25, 1997 and U.S. Pat. No. 5,968,528 to Deckner et al., issued on Oct. 19, 1999, U.S. Pat. No. 4,139,619 to Chidsey, III, issued on Feb. 13, 1979 and U.S. Pat. No. 4,684,635 to Orentreich et al., issued on Aug. 4, 1987 which are incorporated herein by reference. Suitable pharmaceutical carriers are further described in Remington's Pharmaceutical Sciences, 17th ed., Mack Publishing Company, Easton, Pa. (1990) a standard reference text in this field.

The pharmaceutical compositions of the invention may also include optional components. Such optional components should be suitable for application to keratinous tissue, that is, when incorporated into the composition, they are suitable for use in contact with human keratinous tissue without undue toxicity, incompatibility, instability, allergic response, and the like within the scope of sound medical judgment. In addition, such optional components are useful provided that they do not unacceptably alter the benefits of the active compounds of the invention. The CTFA Cosmetic Ingredient Handbook, Second Edition (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyffhizinate), skin treating agents, thickeners, and vitamins and derivatives thereof.

In addition to the pharmaceutically effective amount of the anti-darkening compound or compounds disclosed herein, topical compositions of the present invention also comprise a dermatologically acceptable carrier. The phrase "dermatologically acceptable carrier", as used herein, means that the carrier is suitable for topical application to the skin, i.e., keratinous tissue, has good aesthetic properties, is compatible with the active agents of the present invention and any other components, and will not cause any safety or toxicity concerns. A safe and effective amount of carrier is from about 50% to about 99.99%, preferably from about 80% to about 99.9%, more preferably from about 90% to about 98%, and most preferably from about 90% to about 95% of the composition.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an ophthalmic ointment, an aqueous solution, a lotion or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560, issued to Dickert, et al. Aug. 28, 1973; U.S. Pat. No. 4,421,769, issued to Dixon, et al. Dec. 20, 1983; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain a polyorganosiloxane oil. A preferred water-in-silicone emulsion system is formulated to provide an oxidatively stable vehicle for delivery of a pharmaceutically effective amount of an agent disclosed herein. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compound of the invention in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less, under about one atmosphere of pressure. Examples of non-silicone oils suitable for use in the continuous silicone phase are those well known in the chemical arts in topical personal care products in the form of water-in-oil emulsions, e.g. mineral oil, vegetable oils, synthetic oils, semisynthetic oils, etc.

Useful topical compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention typically comprise from about 25% to about 90%, preferably from about 40% to about 80%, more preferably from about 60% to about 80%, water in the dispersed aqueous phase by weight of the composition.

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371 to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent. The preferred structuring agents of the present invention are selected from the group consisting of stearic acid, palmitic acid, stearyl alcohol, cetyl alcohol, behenyl alcohol, stearic; acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See, McCutcheon's. Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al. issued Dec. 20, 1983; and U.S. Pat. No. 3,755,560. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued Sep. 29, 1992; U.S. Pat. No. 5,151,210 to Steuri et al. issued Sep. 29, 1992; U.S. Pat. No. 5,120,532; U.S. Pat. No. 4,387, 090; U.S. Pat. No. 3,155,591; U.S. Pat. No. 3,929,678; U.S. Pat. No. 3,959,461; McCutcheon's, Detergents & Emulsifiers (North American edition 1979) M.C. Publishing Co.; and Schwartz, et al., Surface Active Agents, Their chemistry and Technology, New York: Interscience Publishers, 1949.

Alternatively, other useful cationic emulsifiers include amino-amides. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

A wide variety of anionic surfactants are also useful herein. See, e.g., U.S. Pat. No. 3,929,678, to Laughlin et al., issued Dec. 30, 1975. In addition, amphoteric and zwitterionic surfactants are also useful herein.

The preferred oil-in-water emulsion comprises from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. See, e.g., Sagarin, Cosmetics, Science and Technology, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an agent described herein. A cream typically comprises from about 5% to about 50%, preferably from about 10% to about 20% of emollient; from about 45% to about 85%, preferably from about 50% to about 75% water; and a pharmaceutically effective amount of an agent described herein.

Ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, Cosmetics, Science and Technology, 2nd Edition, Vol. 1, pp. 72-73 (1972), incorporated herein by reference, and/or an emollient. For example, an ointment may comprise from about 2% to about 10% of an emollient; from about 0.1% to about 2% of a thickening agent; and a pharmaceutically effective amount of an agent described herein.

By way of non-limiting example, 1000 g of topical cream is prepared from the following types and amounts of ingredients: a pharmaceutically effective amount of an agent disclosed herein, tegacid regular (150 g) (a self-emulsifying glyceryl monostearate from Goldschmidt Chemical Corporation, New York, N.Y.), polysorbate 80 (50 g), spermaceti (100 g), propylene glycol (50 g), methylparaben (1 g), and deionized water in sufficient quantity to reach 1000 gm. The tegacid and spermaceti are melted together at a temperature of 70-80° C. The methylparaben is dissolved in about 500 g of water and the propylene glycol, polysorbate 80, and 6-amino-1,2-dihydro-1-hydroxy-2-imino-4-piperidinopyrimidine free base are added in turn, maintaining a temperature of 75-80° C. The methylparaben mixture is added slowly to the tegacid and spermaceti melt, with constant stirring. The addition is continued for at least 30 minutes with additional stirring until the temperature has dropped to 40-45° C. Finally, sufficient water is added to bring the final weight to 1000 g and the preparation stirred to maintain homogeneity until cooled and congealed.

By way of non-limiting example, 1000 g of a topical ointment is prepared from the following types and amounts of ingredients: a pharmaceutically effective amount of an agent disclosed herein, zinc oxide (50 g), calamine (50 g), liquid petrolatum (heavy) (250 g), wool fat (200 g), and enough white petrolatum to reach 1000 g. Briefly, the white petrolatum and wool fat are melted and 100 g of liquid petrolatum added thereto. The pharmaceutically effective amount of an agent disclosed herein, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

By way of non-limiting example, 1000 g of an ointment, e.g., an ophthalmic ointment, containing a pharmaceutically effective amount of an agent disclosed herein is prepared from the following types and amounts of ingredients: a pharmaceutically effective amount of an agent disclosed herein, light liquid petrolatum (250 g), wool fat (200 g), and enough white petrolatum to reach 1000 g. Briefly, the pharmaceutically effective amount of an agent disclosed herein is finely divided and added to the light liquid petrolatum. The wool fat and white petrolatum are melted together, strained, and the temperature adjusted to 45-50° C. The liquid petrolatum slurry is added, and the ointment stirred until congealed.

By way of non-limiting example, 1000 ml of an aqueous solution containing a pharmaceutically effective amount of an agent disclosed herein is prepared from the following types and amounts of ingredients: a pharmaceutically effective amount of an agent disclosed herein, polyethylene glycol 4000 (120 g) myristyl-gamma-picolinium chloride (0.2 g), polyvinylpyrrolidone (1 g), and enough deionized water to reach 1000 milliliters. Briefly, the ingredients are dissolved in the water and the resulting solution is sterilized by filtration.

By way of non-limiting example, 1000 g of lotion containing a pharmaceutically effective amount of an agent disclosed herein is prepared from the following types and amounts of ingredients: a pharmaceutically effective amount of an agent disclosed herein, N-methylpyrolidone (40 g), and enough propylene glycol to reach 1000 g.

By way of non-limiting example, an aerosol containing a pharmaceutically effective amount of an agent disclosed herein is prepared from the following types and amounts of materials: a pharmaceutically effective amount of an agent disclosed herein, absolute alcohol (4.37 g), Dichlorodifluoroethane (1.43 g) and dichlorotetrafluoroethane (5.70 g). Briefly, the pharmaceutically effective amount of an agent disclosed herein is dissolved in the absolute alcohol and the resulting solution filtered to remove particles and lint. This solution is chilled to about −30° C. Then, to this is added the chilled mixture of dichlorodifluoromethane and dichlorotetrafluoroethane.

The following additional formulation examples illustrate representative compositions that may be prepared in accordance with this invention. The present invention, however, is not limited to the following compositions.

Formulation 1

Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color could be diluted with water and added with stirring. Sufficient water may then be added to produce a total volume of 5 mL.

Formulation 2

Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) could be added and the resulting mixture would be stirred until it congeals.

General Methods of Preparation

The compounds of this invention are generally available and can be purchased from commercial sources and tested for their activities. The test compounds which are not commercially available can be prepared from readily available starting materials using various general methods and procedures known in the art. For example, the compounds may be synthetically prepared from known starting materials by conventional laboratory procedures and protocols. Likewise, those compounds that may be found in existing natural materials may be isolated and/or purified by known procedures, to attain the requisite concentration and content of the active, to be efficacious when formulated into compositions in accordance with the present invention. Such preparations may also be described as formulations or materials that are enriched for the particular compound(s) of the invention, and the present invention embraces such preparations within its scope.

Additionally, as will be apparent to those skilled in the art with respect to the methods of preparation of the compounds of the invention involving organic synthesis, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

Example 1

Screening of Compounds in Cultured Murine Melanocytes

The Spectrum Collection library consisting of 2000 drug compounds or natural products represents a source for the identification of compounds useful in the present invention. The library may be screened to identify novel pigmentation inhibitors in cultured murine melanocytes (melan-a). Compounds are dissolved in dimethylsulfoxide (DMSO) to a final concentration of 10 mM. Screening is performed with cultured melanocytes in 24-well plates followed by melanin assay (see below). A minimum change of 50% in melanin formation is established as significant for a pigmentation inhibitor. DMSO may be used as a negative control and the widely used depigmenting agent, hydroquinone, may be used as a positive control on every plate. Primary screening is performed at a final concentration of 1 μM and potential candidates from the primary screening are reconfirmed in duplicate at final concentrations of 1 and 5 μM.

Melan-a cells are plated at $5\times10^4$ cells per well in 1 ml of culture media in 24-well plates the day before adding the library compounds. All compounds are added at the indicated final concentrations. Cells are harvested after 72 hours of incubation, and the melanin assay is performed.

For further test and mechanism of action studies, the compounds may be purchased from Sigma, MicroSource or other known suppliers. The compounds are dissolved in dimethylsulfoxide (DMSO) to a final concentration of 10 mM, and are tested for their effect on melanin synthesis at the indicated final concentrations.

Example 2

Melanin Assay

For the primary and secondary screening, cells were harvested and dissolved in 200 μl of 2N NaOH in 20% DMSO at 70° C. A 180-μl aliquot of the resulting solution was measured for absorbance at 490 nm.

Figure 2:
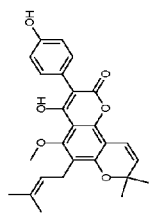
FIG. 2 is a graph of the individual dose response testing of Scandenin, a particular compound of the invention.
Figure 2:
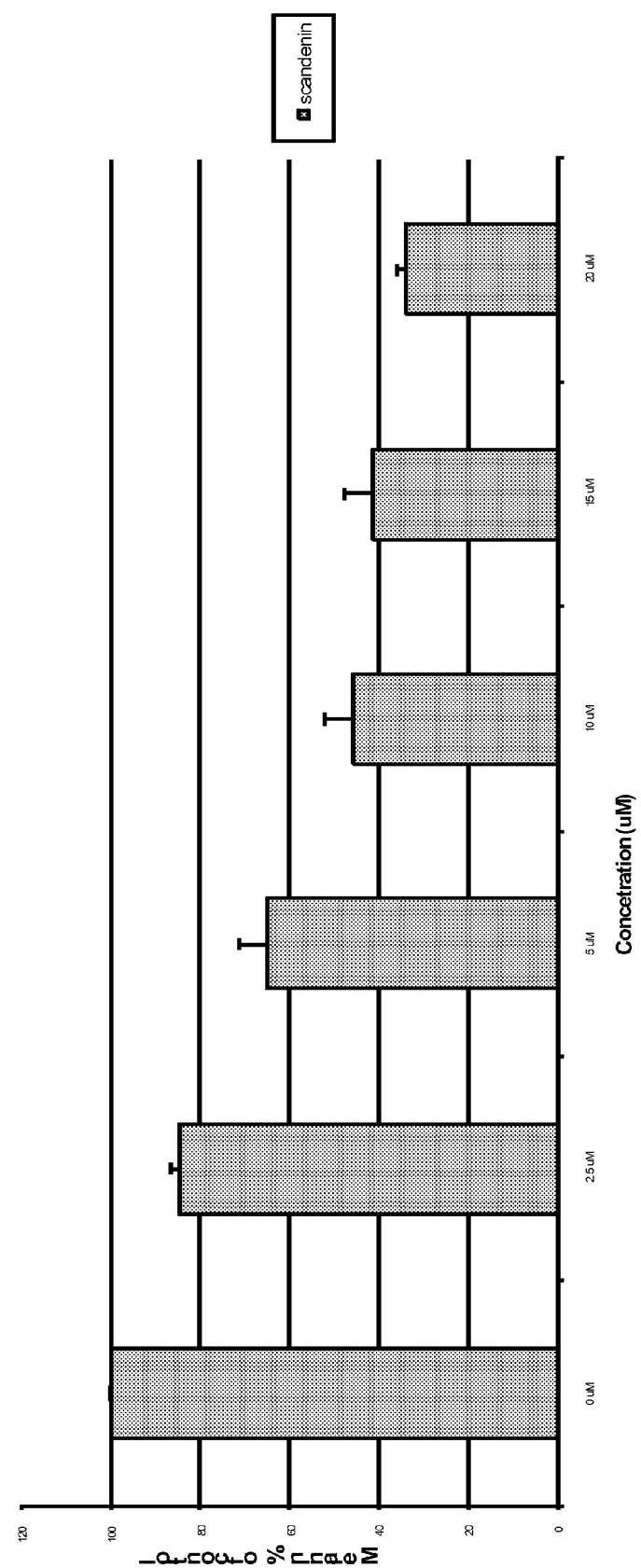

A series of structurally related compounds was then tested in this screen, to identify compounds that inhibit skin darkening. The compounds, their structures, inhibition data expressed as % of control remaining, are shown in Table 1, below. In addition, dose-response data as to scandenin, robustic acid methyl ether, and coumophos are also presented in FIGS. 1-4.

TABLE 1

Skin Darkening Inhibition Data

| ID | Name | Structure | % of control melanin remaining after treatment @ 1 μM | % of control melanin remaining after treatment @ 5 μM |
|---|---|---|---|---|
| 1 | PRENYLETIN | 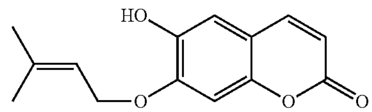 [SMILES: CC(C)=CCOc1cc2oc(=O)ccc2cc1O] | 79 | 80 |
| 2 | OBLIQUIN | 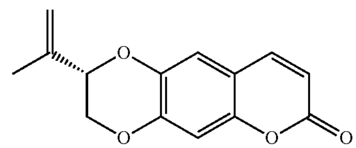 [SMILES: C=C(C)[C@H]1COc2cc3oc(=O)ccc3cc2O1] | 84 | 95 |
| 3 | DIHYDRO-OBLIQUIN | 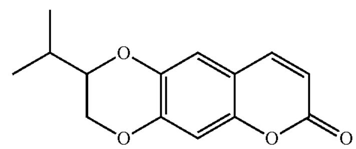 [SMILES: CC(C)C1COc2cc3oc(=O)ccc3cc2O1] | 81 | 81 |
| 4 | FRAXIDIN METHYL ETHER | 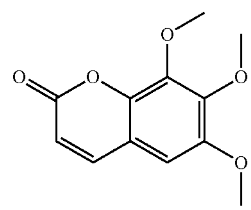 [SMILES: COc1cc2ccc(=O)oc2c(OC)c1OC] | 87 | 95 |
| 5 | XANTHYLETIN | 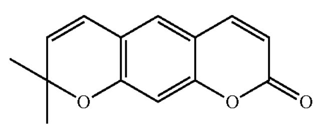 [SMILES: CC1(C)C=Cc2cc3ccc(=O)oc3cc2O1] | 99 | 110 |
| 6 | IMPERATORIN | 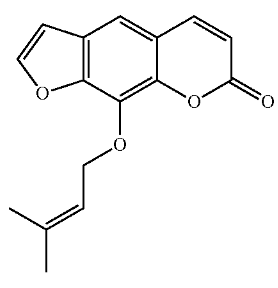 [SMILES: CC(C)=CCOc1c2occc2cc2ccc(=O)oc12] | 91 | 96 |
| 7 | PACHYRRHIZIN | 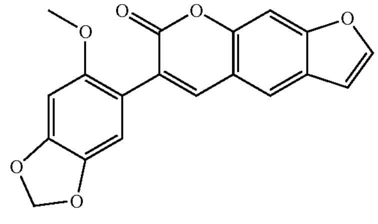 [SMILES: COc1cc2c(cc1-c1cc3cc4ccoc4cc3oc1=O)OCO2] | 75 | 71 |
| 8 | HERNIARIN | 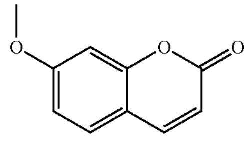 | 84 | 81 |

TABLE 1-continued

Skin Darkening Inhibition Data

| ID | Name | Structure | % of control melanin remaining after treatment @ 1 µM | % of control melanin remaining after treatment @ 5 µM |
|---|---|---|---|---|
| 9 | ROBUSTIC ACID METHYL ETHER | 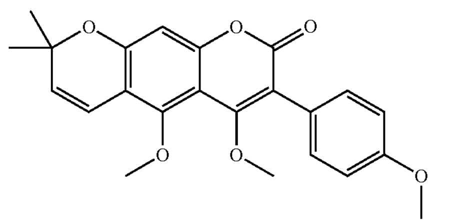 | 69 | 16 |
| 10 | ROBUSTIC ACID | 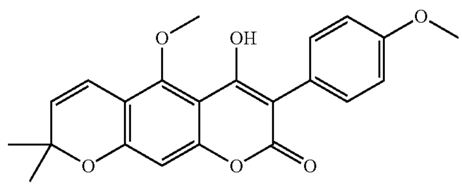 | 91 | 93 |
| 11 | KUHLMANNIN | 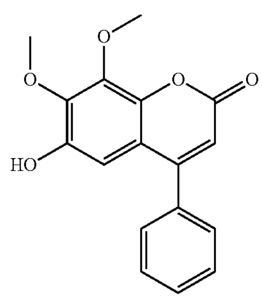 [SMILES: COc1c(O)cc2c(-c3ccccc3)cc(=O)oc2c1OC] | 81 | 84 |
| 12 | SPHONDIN | 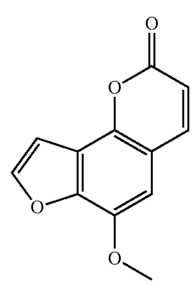 [SMILES: COc1cc2ccc(=O)oc2c2ccoc12] | 89 | 101 |
| 13 | ISOPIMPINELLIN | 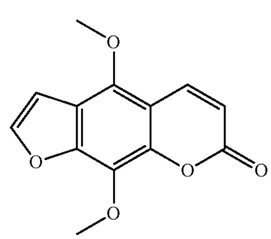 [SMILES: COc1c2ccoc2c(OC)c2oc(=O)ccc12] | 86 | 95 |

TABLE 1-continued

Skin Darkening Inhibition Data

| ID | Name | Structure | % of control melanin remaining after treatment @ 1 μM | % of control melanin remaining after treatment @ 5 μM |
|----|------|-----------|---|---|
| 14 | PIMPINELLIN | 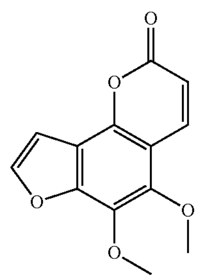 [SMILES: COc1c(OC)c2occc2c2oc(=O)ccc12] | 76 | 109 |
| 15 | ISOBERGAPTENE | 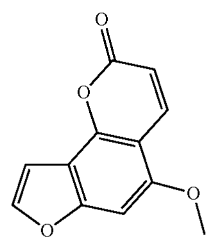 [SMILES: COc1cc2occc2c2oc(=O)ccc12] | 86 | 108 |
| 16 | SCANDENIN | 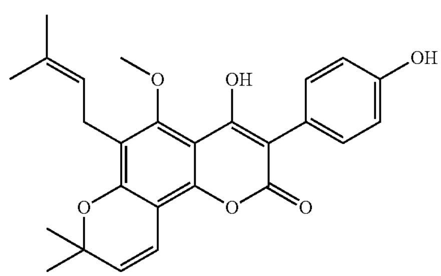 [SMILES: COc1c(CC=C(C)C)c2c(c3oc(=O)c(-c4ccc(O)cc4)c(O)c13)C=CC(C)(C)O2] | 90 | 64 |
| 17 | HYMECROMONE METHYL ETHER | 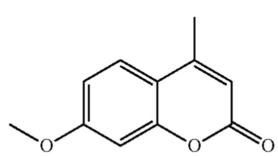 | 96 | 93 |
| 18 | BERGAPTENE | 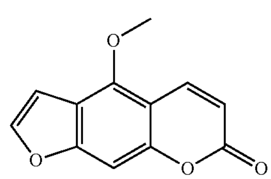 [SMILES: COc1c2ccoc2cc2oc(=O)ccc12] | 100 | 93 |
| 19 | COUMOPHOS | 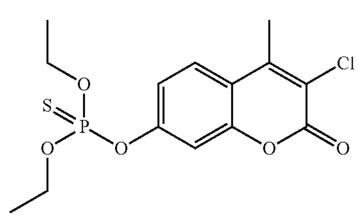 [SMILES: CCOP(=S)(OCC)Oc1ccc2c(C)c(Cl)c(=O)oc2c1] | 81 | 48 |

TABLE 1-continued

Skin Darkening Inhibition Data

| ID | Name | Structure | % of control melanin remaining after treatment @ 1 μM | % of control melanin remaining after treatment @ 5 μM |
|---|---|---|---|---|
| 20 | METHOXSALEN | 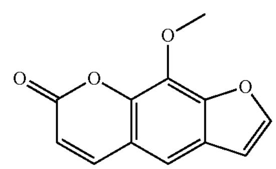 [SMILES: COc1c2occc2cc2ccc(=O)oc12] | 120 | 125 |
| 21 | NOVOBIOCIN SODIUM | 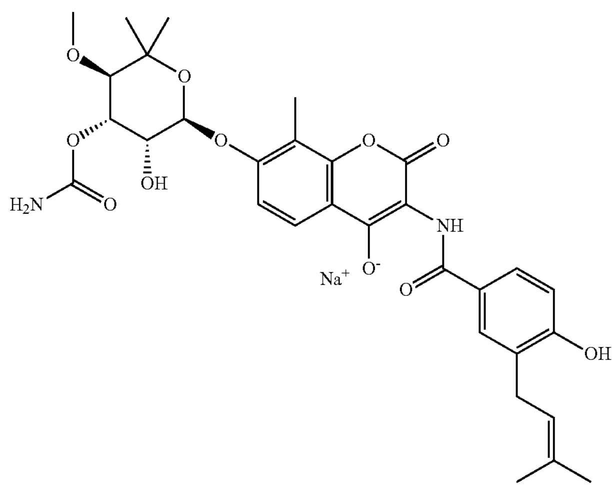 [SMILES: CO[C@@H]1[C@@H](OC(N)=O)[C@@H](O)[C@H](Oc2ccc3c([O-])c(NC(=O)c4ccc(O)c(CC=C(C)C)c4)c(=O)oc3c2C)OC1(C)C ; [Na+]] | 90 | 94 |
| 22 | TRIOXSALEN | 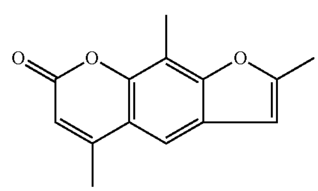 [SMILES: Cc1cc2cc3c(C)cc(=O)oc3c(C)c2o1] | 90 | 118 |
| 23 | CITROPTEN | 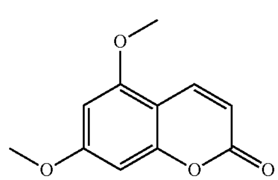 | 86 | 97 |
| 24 | 4-METHYLESCULETIN | 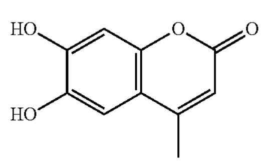 | 88 | 100 |
| 25 | ESCULETIN | 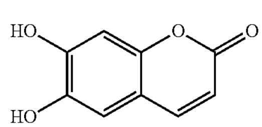 | 87 | 88 |

TABLE 1-continued
Skin Darkening Inhibition Data
| ID | Name | Structure | % of control melanin remaining after treatment @ 1 μM | % of control melanin remaining after treatment @ 5 μM |
|---|---|---|---|---|
| 26 | AESCULIN | 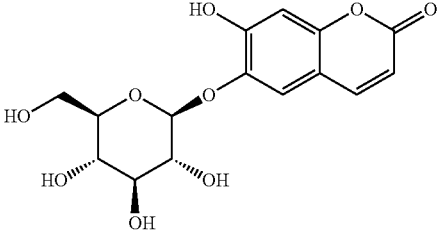 [SMILES: O=c1ccc2cc(O[C@@H]3O[C@H](CO)[C@@H](O)[C@H](O)[C@H]3O)c(O)cc2o1] | 70 | 84 |
| 27 | LOMATIN | 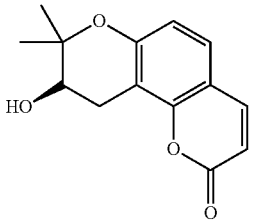 | 89 | 85 |
| 28 | SELINIDIN | 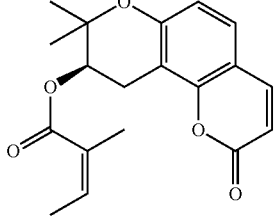 | 85 | 82 |
| 29 | PTERYXIN | 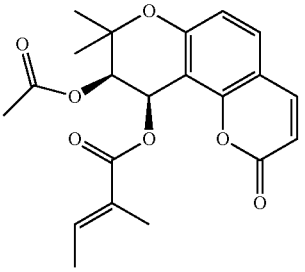 [SMILES: C/C=C(\C)C(=O)O[C@@H]1c2c(ccc3ccc(=O)oc23)OC(C)(C)[C@@H]1OC(C)=O] | 93 | 101 |
| 30 | DIHYDROSAMIDIN | 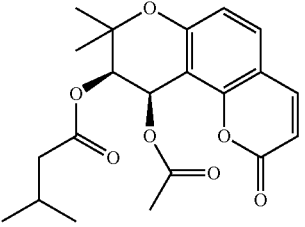 [SMILES: CC(=O)O[C@@H]1c2c(ccc3ccc(=O)oc23)OC(C)(C)[C@@H]1OC(=O)CC(C)C] | 106 | 88 |
| 31 | MARMESIN | 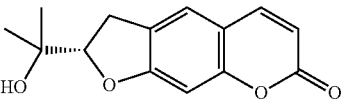 [SMILES: CC(C)(O)[C@@H]1Cc2cc3ccc(=O)oc3cc2O1] | 89 | 97 |

TABLE 1-continued

Skin Darkening Inhibition Data

| ID | Name | Structure | % of control melanin remaining after treatment @ 1 μM | % of control melanin remaining after treatment @ 5 μM |
|---|---|---|---|---|
| 32 | MARMESIN ACETATE | 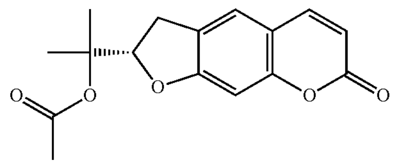 [SMILES: CC(=O)OC(C)(C)[C@@H]1Cc2cc3ccc(=O)oc3cc2O1] | 77 | 92 |
| 34 | PEUCEDANIN | 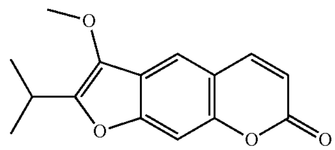 [SMILES: COc1c(C(C)C)oc2cc3oc(=O)ccc3cc12] | 83 | 84 |
| 35 | LONCHOCARPIC ACID | 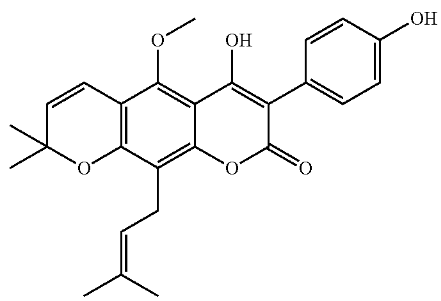 [SMILES: COc1c2c(c(CC=C(C)C)c3oc(=O)c(-c4ccc(O)cc4)c(O)c13)OC(C)(C)C=C2] | 84 | 81 |
| 36 | DERRUSNIN | 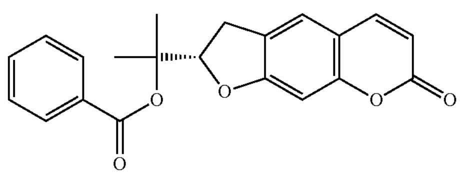 [SMILES: CC(C)(OC(=O)c1ccccc1)[C@@H]1Cc2cc3ccc(=O)oc3cc2O1] | 81 | 87 |
| 37 | 4-METHYLDAPHNETIN | 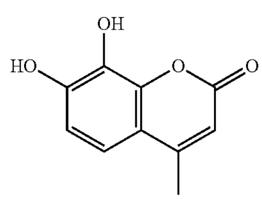 | 83 | 88 |
| 38 | SCOPOLETIN | 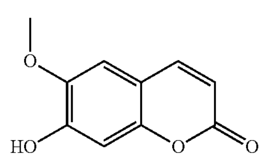 | 77 | 83 |
| 39 | FRAXETIN | 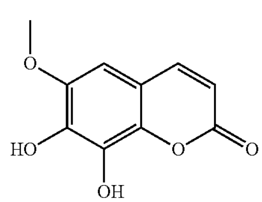 | 84 | 89 |

TABLE 1-continued

Skin Darkening Inhibition Data

| ID | Name | Structure | % of control melanin remaining after treatment @ 1 μM | % of control melanin remaining after treatment @ 5 μM |
|----|------|-----------|---|---|
| 40 | FELAMIDIN | 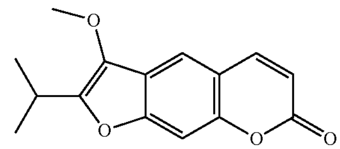 [SMILES: COc1c(C(C)C)oc2cc3oc(=O)ccc3cc12] | 97 | 88 |

As the assay above compares the accumulation of melanin in cells treated only with carrier (DMSO) versus those treated with 1 and 5 uM test compound, it can be seen that compounds 7, 9, 16, 19 and 33 show a robust dose dependent ability to block melanin accumulation, thus leading to the discovery of these compounds as agents capable of blocking skin darkening.

Example 3

MelanoDerm Pigmentation Assay

The compounds of the invention may be tested in the MelanoDerm™ pigmentation assay, to confirm and demonstrate their activity as inhibitors in a setting that replicates in vivo conditions. MelanoDerm™, made by MatTek Corp., is a viable reconstituted three-dimensional human skin equivalent containing normal melanocytes and keratinocytes that are derived from African-American (MEL-B), Asian (MEL-A) or Caucasian (MEL-C) donors. Both MEL-A and MEL-B tissues are used in the study, and they are maintained in the NMM-113 medium as recommended by the manufacturer.

The test compound is dissolved in 30% ethanol: 70% propylene glycol to a final concentration of 1.0 mM (equal to 356.6 μg/ml), and this is maintained constant and used on all samples tested. A 25 μl of its aliquot is applied topically to the MelanoDerm™ tissue (MEL-B) on Days 0, 1, 3, 6, 8 and 10. The MelanoDerm™ tissues are fed every other day with 5 ml fresh NMM-113. Prior to each application, the tissues are washed with 1 ml PBS to remove any residual test compound. Tissues are fixed on Days 10 and 13 for microscopic analysis and histological evaluation. In addition, duplicate tissues are frozen on Days 10 and 13 for the melanin assay.

Similar experiments may be performed on Asian skin equivalent (MEL-A) except: the treatments are applied on Days 0, 1, 3, 6, 8, 10 and 13. Tissues are taken out on Days 13 and 16 for the various assays. 30% ethanol: 70% propylene glycol is used as a negative control and the well-known pigmentation inhibitor, arbutin (at concentration of 3 mg/ml), may be used as a positive control.

The experiments are repeated twice on both MEL-A and MEL-B tissues from different lots to make sure that the results are reproducible (study 1 or 2). For each experiment, six tissues are treated with a compound or extract of the invention, and six were treated with vesicle (30% ethanol: 70% PEG) or arbutin if applicable. For MEL-B, on day 10, three tissues under each treatment condition are taken out, and one was used for histological studies and the other two are used for the melanin assay. The same protocol is followed with the MEL-B samples after 13 days' treatment and MEL-A after either 13 or 16 days' treatments.

For the histological studies:

Procedure 1: the effects of the inventive compounds or extract on melanin synthesis in MEL-A or B are evaluated by light microscopy (views from the top surface of the tissue).

Procedure 2: the distribution of melanin in the treated-MEL-A or B is accessed by image analysis using Fontana-Masson stained histological sections (views from the side of the tissue).

For the melanin tissues, the melanin content of each individual tissue is determined, and the final data show the average melanin content of 2 tissues treated under identical conditions.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

The chemical names of compounds given in this application were generated using various commercially available chemical naming software tools including MDL's ISIS Draw Autonom Software tool, and were not verified. Particularly, in the event of inconsistency, the depicted structure governs.

What is claimed is:

1. A method for preventing the hyperpigmentation or undesired darkening of skin comprising administering to a subject in need thereof an effective amount of either lonchocarpic acid or a compound of formulae IIIa, IIIb, IIIc or IIId:

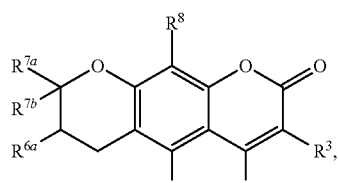
IIIa

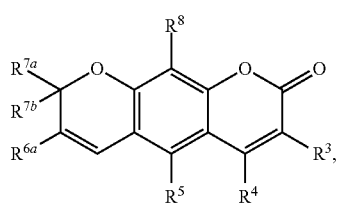
IIIb

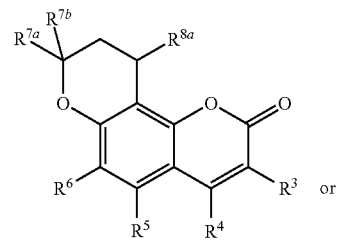
IIIc or

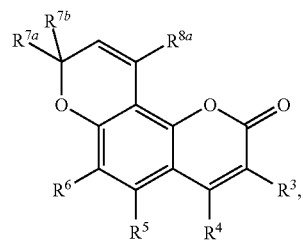
IIId or a pharmaceutically acceptable salt, solvate or prodrug thereof, and stereoisomers, tautomers and isotopic variants thereof; and wherein R⁴ is selected from H, halo, hydroxy, alkoxy, alkenyloxy, substituted or unsubstituted alkyl, substituted or unsubstituted alkenyl, and substituted or unsubstituted phenyl;

R⁵ and R⁶ are independently selected from H, halo, hydroxy, alkoxy, alkenyloxy, substituted or unsubstituted alkyl, substituted or unsubstituted alkenyl, and substituted or unsubstituted phenyl;

R³ is selected from halo, substituted or unsubstituted alkyl, substituted or unsubstituted alkenyl, phenyl, 3,4-dihydroxyphenyl, 4-methoxyphenyl, or 3,4-dimethoxyphenyl;

R⁸ is selected from H, halo, hydroxy, alkoxy, alkenyloxy, substituted or unsubstituted alkyl, substituted or unsubstituted alkenyl, or substituted or unsubstituted phenyl; and each $R^{6a}$, $R^{7a}$ and $R^{7b}$ is independently selected from H, alkyl, hydroxyalkyl, or alkenyl.

2. A method for preventing the hyperpigmentation or undesired darkening of skin comprising administering to a subject in need thereof an effective amount of a compound of formula IV

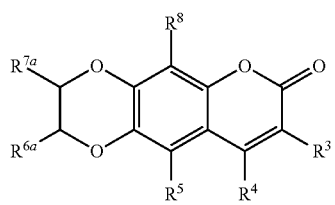
IV or a pharmaceutically acceptable salt, solvate or prodrug thereof, and stereoisomers, tautomers and isotopic variants thereof;

and wherein

R⁴ is selected from H, halo, hydroxy, alkoxy, alkenyloxy, substituted or unsubstituted alkyl, substituted or unsubstituted alkenyl, and substituted or unsubstituted phenyl;

R⁵ is selected from H, halo, hydroxy, alkoxy, alkenyloxy, substituted or unsubstituted alkyl, substituted or unsubstituted alkenyl, and substituted or unsubstituted phenyl;

R³ is selected from halo, substituted or unsubstituted alkyl, substituted or unsubstituted alkenyl, phenyl, 3,4-dihydroxyphenyl, 4-methoxyphenyl, or 3,4-dimethoxyphenyl;

R⁸ is selected from H, halo, hydroxy, alkoxy, alkenyloxy, substituted or unsubstituted alkyl, substituted or unsubstituted alkenyl, or substituted or unsubstituted phenyl;

and each $R^{6a}$ and $R^{7a}$ is independently selected from H, alkyl, or alkenyl.

3. A method for preventing the hyperpigmentation or undesired darkening of skin comprising administering to a subject in need thereof an effective amount of either lonchocarpic acid or a compound of formulae Va, Vb, Vc, or Vd:

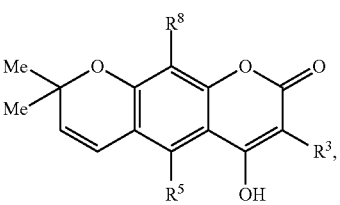
Va

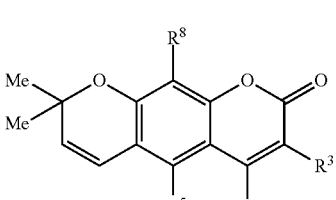
Vb

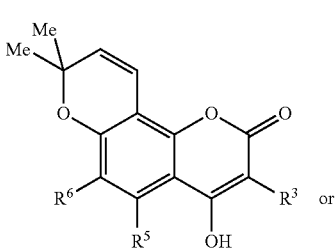
Vc or

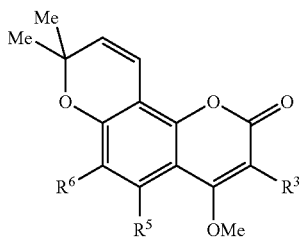

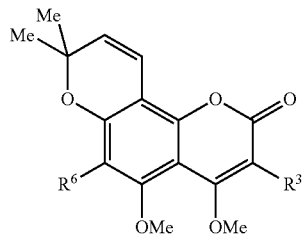

or a pharmaceutically acceptable salt thereof, and stereoisomers, tautomers and isotopic variants thereof; and wherein $R^4$ is selected from H, halo, hydroxy, alkoxy, alkenyloxy, substituted or unsubstituted alkyl, substituted or unsubstituted alkenyl, and substituted or unsubstituted phenyl;

$R^5$ and $R^6$ are independently selected from H, halo, hydroxy, alkoxy, alkenyloxy, substituted or unsubstituted alkyl, substituted or unsubstituted alkenyl, and substituted or unsubstituted phenyl;

$R^3$ is selected from halo, substituted or unsubstituted alkyl, substituted or unsubstituted alkenyl, phenyl, 3,4-dihydroxyphenyl, 4-methoxyphenyl, or 3,4-dimethoxyphenyl;

$R^8$ is selected from H, halo, hydroxy, alkoxy, alkenyloxy, substituted or unsubstituted alkyl, substituted or unsubstituted alkenyl, or substituted or unsubstituted phenyl.

4. A method for preventing the hyperpigmentation or undesired darkening of skin comprising administering to a subject in need thereof an effective amount of a compound of formulae VIa, VIb, VIc, or VId

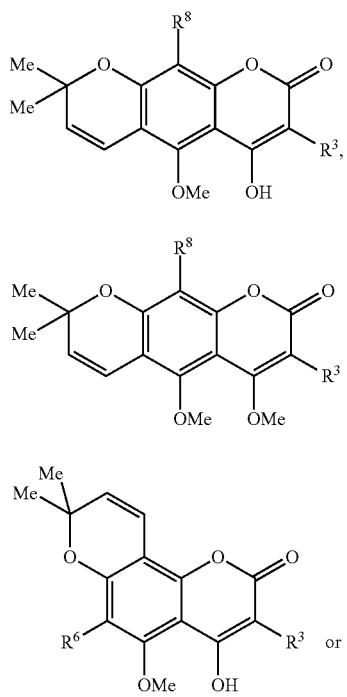

or a pharmaceutically acceptable salt thereof, and stereoisomers, tautomers and isotopic variants thereof; and wherein $R^3$ is selected from halo, substituted or unsubstituted alkyl, substituted or unsubstituted alkenyl, phenyl, 3,4-dihydroxyphenyl, 4-methoxyphenyl, or 3,4-dimethoxyphenyl;

and $R^8$ is selected from H, halo, hydroxy, alkoxy, alkenyloxy, substituted or unsubstituted alkyl, substituted or unsubstituted alkenyl, and substituted or unsubstituted phenyl.

5. A method for preventing the hyperpigmentation or undesired darkening of skin comprising administering to a subject in need thereof an effective amount of a compound of formula VIIa:

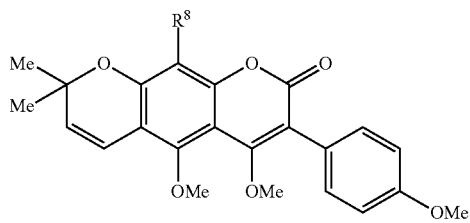

or a pharmaceutically acceptable salt thereof, and stereoisomers, tautomers and isotopic variants thereof; and wherein $R^8$ are as in claim 1.

6. The method of claim 1, wherein the compound is robustic acid methyl ether.

7. The method of claim 1, wherein the method comprises a step of contacting skin with
   a) a composition comprising a compound as defined in claim 1 in a sufficient amount to prevent the hyperpigmentation or undesired darkening of skin, and
   b) an acceptable carrier.

8. A composition for preventing the hyperpigmentation or undesired darkening of skin comprising a pharmaceutically acceptable carrier and a pharmaceutically effective amount of a compound as defined in claim 1.

9. The composition of claim 7 wherein the carrier is a parenteral carrier, oral or topical carrier.

10. A topical formulation, comprising a composition for cosmetic or dermatological use, said composition comprising a compound as defined in claim 1, and an acceptable carrier; and wherein the cosmetic or dermatological use is associated with the prevention of the hyperpigmentation or undesired darkening of skin.

11. A topical formulation for use in personal care or hygiene which includes a personal care or hygiene promoting agent, and a carrier therefor, wherein said formulation includes a skin darkening inhibitor comprising a compound as defined in claim 1.

12. The composition of claim 8, wherein the composition is selected from skin lotion, skin softener, skin toner, astringent, lotion, milk lotion, moisture lotion, nutrient lotion, massage cream, nutrient cream, moisture cream, hand cream, foundation, essence, nutrient essence pack, cleansing foam, cleansing lotion, cleansing cream, body lotion, body cleanser, deodorant, antiperspirant, treatment or beauty solution.

13. A combination to prevent the hyperpigmentation or undesired darkening of skin consisting of a compound as defined in claim 1 and a like-acting agent.

14. The combination of claim 13, wherein said like acting agent is selected from a cosmetic ingredient and a pharmacologically active agent.

15. The combination of claim 14, wherein said pharmacologically active agent is selected from another skin darkening inhibitor.

* * * * *